United States Patent
Mouridsen et al.

(10) Patent No.: US 10,660,597 B2
(45) Date of Patent: May 26, 2020

(54) METHOD FOR ESTIMATING PERFUSION INDICES

(71) Applicant: Aarhus Universitet, Aarhus C (DK)

(72) Inventors: Kim Mouridsen, Hjortshøj (DK); Mikkel Bo Hansen, Skanderborg (DK); Irene Klærke Mikkelsen, Horsens (DK); Susanne Lise Bekke, Solrød Strand (DK); Birgitte Fuglsang Kjølby, Risskov (DK)

(73) Assignee: Aarhus Universitet, Aarhus C (DK)

( * ) Notice: Subject to any disclaimer, the term of this patent is extended or adjusted under 35 U.S.C. 154(b) by 991 days.

(21) Appl. No.: 15/022,786

(22) PCT Filed: Sep. 19, 2014

(86) PCT No.: PCT/DK2014/050296
§ 371 (c)(1),
(2) Date: Mar. 17, 2016

(87) PCT Pub. No.: WO2015/039670
PCT Pub. Date: Mar. 26, 2015

(65) Prior Publication Data
US 2016/0228085 A1    Aug. 11, 2016

(30) Foreign Application Priority Data
Sep. 19, 2013    (EP) .................................... 13185195

(51) Int. Cl.
*A63F 9/24*    (2006.01)
*A61B 6/00*    (2006.01)
(Continued)

(52) U.S. Cl.
CPC ............ *A61B 6/507* (2013.01); *A61B 5/0263* (2013.01); *A61B 6/032* (2013.01); *A61B 6/037* (2013.01);
(Continued)

(58) Field of Classification Search
CPC ....... A61B 6/507; A61B 6/504; A61B 5/0263; A61B 6/032
See application file for complete search history.

(56) References Cited

U.S. PATENT DOCUMENTS

2007/0167731 A1    7/2007   Taxt et al.
2009/0297008 A1*  12/2009   Taxt ...................... G06T 7/0012
                                                    382/131
(Continued)

FOREIGN PATENT DOCUMENTS

WO    WO 2012/130248 A1    10/2012
WO    WO 2012/130249 A1    10/2012

OTHER PUBLICATIONS

Chappell, Michael A. et al., "Variational Bayesian Inference for a Nonlinear Forward Model" IEEE Transactions on Signal Processing, Jan. 2009, pp. 223-236, vol. 57, No. 1.
(Continued)

*Primary Examiner* — Steve Rowland
(74) *Attorney, Agent, or Firm* — Woodard, Emhardt, Henry, Reeves & Wagner, LLP

(57) ABSTRACT

The present invention relates to a method for estimating perfusion indices (PI) in a mammal (200), e.g. a human. Data (DAT, DAT') representative of a contrast agent concentration as a function of time of an injected contrast agent is obtained from a medical imaging system (100). Perfusion indices (PI) are found by applying a parametric model (PM) for capillary transit time distributions as a function of time, and a minorize-maximization (MM) type procedure, such as an expectation-maximization (EM) type procedure, with regularization. The minorize-maximization type procedure has an exact analytical expression for the variance of an observation error of the contrast agent ($C_\varepsilon$) in a non-linear observation model for the contrast agent concentration used in the maximization step. Clinical tests performed for 7
(Continued)

patients show improved MTT mapping as compared to singular value decomposition (SVD), and reduced sensitivity to delay.

22 Claims, 14 Drawing Sheets

(51) Int. Cl.

| | |
|---|---|
| A61B 8/06 | (2006.01) |
| A61B 8/08 | (2006.01) |
| A61B 6/03 | (2006.01) |
| A61B 5/026 | (2006.01) |
| G01R 33/563 | (2006.01) |
| A61B 5/00 | (2006.01) |
| G01R 33/56 | (2006.01) |
| A61B 8/00 | (2006.01) |

(52) U.S. Cl.
CPC .............. *A61B 6/501* (2013.01); *A61B 6/504* (2013.01); *A61B 6/5217* (2013.01); *A61B 8/06* (2013.01); *A61B 8/481* (2013.01); *G01R 33/56366* (2013.01); *A61B 5/4064* (2013.01); *A61B 6/481* (2013.01); *A61B 6/583* (2013.01); *A61B 8/5223* (2013.01); *A61B 8/587* (2013.01); *A61B 2576/026* (2013.01); *G01R 33/5601* (2013.01)

(56) References Cited

U.S. PATENT DOCUMENTS

2011/0257519 A1* 10/2011 Bj?rnerud .............. A61B 5/055
600/431
2012/0141005 A1* 6/2012 Djeridane .......... A61B 5/02028
382/131

OTHER PUBLICATIONS

Dempster, A.P. et al., "Maximum Likelihood from Incomplete Data via the EM Algorithm" Journal of the Royal Statistical Society, 1977, pp. 1-38, vol. 39, No. 1.

Jespersen, Sune N. et al., "The Roles of cerebral blood flow, capillary transit time heterogeneity, and oxygen tension in brain oxygenation and metabolism" Journal of Cerebral Blood Flow & Metabolism, 2012, pp. 264-277, vol. 32.

Kalicka, Renata et al., "Parametric Modeling of DSC-MRI Data with Stochastic Filtration and Optimal Input Design Versus Non-Parametric Modeling" Annals of Biomedical Engineering, Mar. 2007, pp. 453-464, vol. 35, No. 3.

Mikkelsen, Irene Klærke et al., "Feasibility of CTTH measurements using Computerized Tomography" Poster—University of Aarhus / Aarhus University Hospital—Center of Functionally Integrative Neuroscience.

Mouridsen, Kim et al., "Bayesian estimation of cerebral perfusion using a physiological model of microvasculature" NeuroImage, 2006, pp. 570-579, vol. 33.

Mouridsen, K. et al., "Reliable estimation of capillary transit time distributions at voxel-level using DSC-MRI" Proc. Intl. Soc. Mag. Reson. Med., 2011, p. 3915, vol. 19.

Østergaard, Leif et al., "The capillary dysfunction hypothesis of Alzheimer's disease" Neurobiology, 2013, pp. 1018-1031, vol. 34.

Østergaard, Leif et al., "The role of the cerebral capillaries in acute ischemic stroke: the extended penumbra model" Journal of Cerebral Blood Flow & Metabolism, 2013, pp. 635-648, vol. 33.

Wu, Yu-Te et al., "Classification of Spatiotemporal Hemodynamics From Brain Perfusion MR Images Using Expectation-Maximization Estimation With Finite Mixture of Multivariate Gaussian Distributions" Magnetic Resonance in Medicine, 2007, pp. 181-191, vol. 57.

International Search Report for PCT/DK2014/050296 dated Nov. 27, 2014.

* cited by examiner

METHOD FOR ESTIMATING PERFUSION INDICES

CROSS REFERENCE TO RELATED APPLICATIONS

This application is a U.S. National Phase Application of PCT International Application Number PCT/DK2014/050296, filed on Sep. 19, 2014, designating the United States of America and published in the English language, which is an International Application of and claims the benefit of priority to European Patent Application No. 13185195.8, filed on Sep. 19, 2013. The disclosures of the above-referenced applications are hereby expressly incorporated by reference in their entireties.

FIELD OF THE INVENTION

The present invention relates to a method for estimating perfusion indices in a mammal, e.g. blood flow, a corresponding medical imaging system, and a corresponding computer program product capable of implementing the invention.

BACKGROUND OF THE INVENTION

The process of blood passing through the tissues is called perfusion and is one of the most fundamental physiological quantifiables. Disorder of perfusion is a process leading to mammal disease and mortality.

Normal brain function requires a continuous supply of oxygen to meet the metabolic demands of activity. The regional availability of oxygen in brain tissue is traditionally inferred from the magnitude of cerebral blood flow (CBF) and the concentration of oxygen in arterial blood. CBF is sensitive to regional levels of neuronal activity—known as neurovascular coupling—and methods to detect changes in CBF therefore provide powerful means of mapping brain function.

In disease, measurements of CBF are widely used in the evaluation of patients suspected of acute ischemic stroke and in patients with flow-limiting steno-occlusive diseases of their carotid arteries, due to well-defined thresholds for sustaining neuronal firing and development of permanent infarction.

The standard method of estimating CBF is currently singular value decomposition (SVD), available in several variants. In short, the SVD technique for estimating CBF is essentially based on deconvolving the arterial input function (AIF) with the concentration time curve using singular value decomposition (SVD) to estimate the impulse response (defined as the residue function multiplied by CBF). Its maximum value is then the CBF.

However, SVD is known to underestimate high flow components and to be sensitive to delays in the arterial input function (AIF), which may compromise physiological interpretation of the perfusion indices obtained by SVD. Needless to say, this could be very critical for the diagnosis of patients having a severe condition, e.g. acute stroke where CBF is used is to delineate the ischemic regions.

Recently, Kim Mouridsen et al., NeuroImage, 33 (2006), 570-579, proposed an alternative model approach using a physiological model of the transport in the capillaries. Using Bayesian modeling, an estimate of hemodynamic parameters can be obtained. More specifically, a parametric model of the residue function with a gamma-type function is used. The obtained results compare well to the SVD methods for low flows, but do not underestimate high flows and is comparatively not as affected by noise as SVD. However, the results are still somewhat sensitive to noise and rely on general numerical approximation schemes which may compromise precision of estimates and result in clinically infeasible computing times, thus limiting practical implementation.

Hence, an improved method for estimating perfusion indices would be advantageous, and in particular a more efficient and/or reliable method for estimating perfusion indices would be advantageous.

SUMMARY OF THE INVENTION

It is an object of the present invention to provide an alternative to the prior art.

In particular, it may be seen as an object of the present invention to provide a method for estimating perfusion indices that solves the above mentioned problems of the prior art with perfusion indices having an insufficient robustness against noise and/or the perfusion indices requiring long imaging/measurement time.

Thus, the above described object and several other objects are intended to be obtained in a first aspect of the invention by providing a method for estimating perfusion indices (PI) in a mammal by a processor, the method comprising:
  obtaining data representative of a contrast agent concentration as a function of time of an injected contrast agent, and
  estimating perfusion indices by:
    applying a parametric model (PM) for capillary transit time distributions as a function of time on the obtained data, and
    applying a minorize-maximization (MM) type procedure, preferably an expectation-maximization (EM) type procedure, with regularization for estimating of the perfusion indices by an optimization,
  wherein the minorize-maximization type procedure, preferably the expectation-maximization type procedure, comprises an exact analytical expression for the variance of an observation error of the contrast agent ($C_\varepsilon$) in a non-linear observation model for the contrast agent concentration used in the maximization step.

The invention is particularly, but not exclusively, advantageous for obtaining perfusion indices in a more efficient and/or reliable manner. The advantages of the invention particularly include:
  improved estimation of perfusion indices on actual patients as compared to state of the art SVD estimates,
  reduction of scan time in e.g. acute stroke because ischemic lesions can be detected with fewer image acquisitions,
  better correspondence between neurological score and imaging in acute strokes,
  more physiologically feasible and robust estimates of capillary transit time distribution,
  fewer patients required for clinical trials since high discriminatory ability of this technique in detecting capillary flow levels translates into higher statistical power, and
  less sensitivity for delay of the contrast agent arrival on the perfusion indices.

These and other advantages will be further explained and illustrated in more detail below.

In the context of the present invention, it should be noted that obtaining data representative of a contrast agent concentration as a function of time of an injected contrast agent is distinct and separate from the process of injecting the contrast agent itself. The present invention is not intended to include the process of injecting the contrast agent, and for practical purposes the obtaining of such data is typically performed a significant amount of time after the injection of contrast agent in the mammal being examined. It should also be noted that injection of a contrast agent is typically a standard medical procedure, and hence not associated with a significant health risk.

Perfusion indices, also called perfusion markers or hemodynamic parameters, are in the context of the present invention not limited to conventional indices, e.g. cerebral blood flow (CBF), cerebral blood volume (CBV) or mean transit time (MIT), but also other perfusion indices where it may be appropriately defined, e.g. capillary transit heterogeneity (CTH or CTTH) indicative of inhomogeneous blood flow of the capillary distribution, or oxygen extraction capacity (OEC) relating to the maximum amount of oxygen which can be extracted from the capillaries.

The invention may be applied for estimating perfusion indices for any mammal, including, but not limited to, humans, monkeys, horses, cows, pigs, rodents, etc., both for testing, e.g. pre-clinic testing, and clinical purposes.

The invention may be applied for estimating perfusion indices for any part of the body, including, but not limited to, the brain, the kidneys, the liver, the heart, parts of a muscle, etc., where perfusion occur in a body.

In the context of the present invention, it is to be understood that the term "estimating" is to be interpreted broadly, and it may include obtaining a direct and/or indirect measure of one or more perfusion indices. This includes in particular an approximate measure of one or more indices.

In the context of the present invention, it is also to be understood that the term "parametric model (PM) for capillary transit time distributions as a function of time" is to be construed broadly as a physiological model for capillary transit distribution depending on one or more parameters i.e. a choice of model is made for the blood flowing through a capillary region over time. The actual choice of a model depends on a number of factors, including, but not limited to, medical imaging modality for obtaining data, kind of disease and/or tissue type being imaged, computational time/accuracy/precision/robustness/convergence, etc. It is contemplated that for some applications, several qualitative different models may be applied and/or compared.

In the present context, the terms "capillary region", "capillary structure" and "capillary bed" refer to an interweaving network of capillaries supplying a specified part of an organ or a tissue. The capillary bed may, in the context of present invention, have various spatial extensions depending of the nature of the means applied for obtaining data representative for the contrast agent concentration through the capillary bed; and/or the nature of the means for measuring data representative for the contrast agent concentration in a capillary bed, and/or on the tissue being measured upon.

The capillary bed or structure consists of a network of capillaries having a basic dimension in the micro-meter range, typical brain capillary has for instance a length of 120 micrometer and 8 micrometer in diameter. The extension of the capillary bed will therefore be limited from below by the need for measuring on a plurality of capillaries to derive a meaningful measure of the data representative for the contrast agent concentration. Similarly, the extension of the capillary bed will typically be limited by the available spatial resolution of the measurement means applied for measuring data representative for the contrast agent concentration as will readily be appreciated by the skilled person working with medical imaging techniques. Working for example with magnetic resonance imaging (MRI or MR) will currently yield a spatial resolution in the order of sub-millimetres, whereas some optical detection techniques, e.g. two-photon microscopy imaging, are strictly speaking only limited by the diffraction limit ($\cdot\lambda/2$, $\lambda$ being the wave-length of the probing radiation), this limit being typically smaller than the spatial extension of a single capillary and thus measuring or averaging over more capillaries may be necessary.

Within numerical analysis, it is well-known that a minorize-maximization (MM) type problem can usually be redefined as a corresponding majorize-maximization (MM) type problem. In the present context, the invention is formulated merely for clarity as a minorize-maximization type model, e.g. expectation maximization (EM), but as it will be readily understood by the skilled person in numerical analysis, the teaching and principle of the present invention can similarly include also majorize-minimization (MM) type models. For further details on this duality, the skilled reader is referred to *Numerical Analysis for Statisticians*, Kenneth Lange, 2010, Springer, (particular pages 189-221), which is hereby incorporated by reference in its entirety.

The expectation maximization (EM) procedure is known from numerical analysis as a special kind of minorize-maximization (MM) procedure, which is particularly useful when no closed form of likelihood equations is available but rather an iterative estimation of maximum likelihood is available. At the core of an EM procedure is some notion of missing data (failure to record, or theoretically missing). One can think of the expectation step of the EM algorithm as 'filling in' the missing data. Because the surrogate function is typically simpler to find than the likelihood itself, the M step can often be performed analytically. The price is, however, that iteration has to be performed. The present invention is particular in that an exact analytical form of an observation error is used in the maximization step, which significantly improves calculations as it will be explained in further detail below. For further details on the EM procedure in general, the skilled reader is referred to *Numerical Analysis for Statisticians*, Kenneth Lange, 2010, Springer, (pages 223-247), which is hereby incorporated by reference in its entirety.

In numerical analysis, it is often required to perform a so-called regularization in order to solve an ill-posed problem or prevent over-fitting by providing additionally constraining information. This present invention is also implemented with regularization, though it is also contemplated that the invention for some embodiment may work without. Generally, Bayesian models may apply regularization by imposed constrains on the model parameters. Particularly, the regularization may be facilitated through the prior expectation and variance of the perfusion parameters. Since these quantities can be obtained empirically from perfusion measurements, this may be a physiologically more appropriate approach to regularization than normally performed for SVD, where the oscillations of the residue function are limited.

In the context of the present invention, it is to be understood that the term "exact analytical expression" should be interpreted in a broad sense. The term is particularly intended to mean, but not limited to, a closed mathematical formula for the variance of the observation error of the contrast agent, which directly and unambiguously can produce a variance value. This is normally opposite to a numerical expression, which only provides an approximate value, or an implicit description of the value, which can only be obtained through iterations. Thus, there is no need for numerical approximation, iteration or further mathematical procedures for producing a variance value with the present invention.

In the context of the present invention, it is further to be understood that the term "contrast agent" is to be interpreted in a broad manner, particularly interpreted as including, but not limited to, the terms "bolus", "bolus agent", "tracer" and/or "tracer agent" or any technical equivalents thereof as the skilled person in medicine or medical imaging will readily understand considering the principle and teaching of the present invention.

In the context of the present invention, it is moreover to be understood that the term "contrast agent leakage" is to be interpreted broadly as the leakage of contrast agent from the vasculature to the extravascular, extracellular space, e.g. in the event of a non-intact vessel. This could for example be the breakdown, puncture, or perforation of the blood-brain-barrier or loss of integrity of the tight endothelial junctions. It also pertains to the kinetics of tissue outside the central nervous system, where no blood-brain barrier exists. The backflow from the extravascular extracellular space to the vascular territory is not included in most embodiments, as this happens on a much longer timescale compared to what is standard in clinical measurements. For instance, a typical acute MRI scan is on the order of a minute, while the backflow is on the order 5-10 minutes or more.

In one embodiment, the parametric model (PM) for capillary transit time distributions as a function of time may comprise at least two parameters, optionally at least three parameters, the model further being defined for positive, or zero, transit times. Alternatively, only two parameters may be applied, more alternatively only three parameters may be applied for the present invention. The low number of parameters facilitates simple and therefore fast computational implementation while at the same time being a realistic model of the physiology. Particularly, the parametric model (PM) for capillary transit time distributions as a function of time may be selected from the non-exhaustive group consisting of: gamma distribution, F-distribution, inverse Gaussian distribution, Gaussian distribution, half-normal distribution, Rayleigh distribution, Weibull distribution, negative binomial distribution, Poisson distribution, Boltzmann distribution, or any combinations thereof, or any equivalents derived thereof.

In an advantageous embodiment, the parametric model (PM) for capillary transit time distributions may a gamma-type function as a function of time (Γ(t) so as to enable estimation of a residue function, R(t), preferably on the form:

$$h(t \mid \alpha, \beta) = -\frac{dR}{dt} = \frac{1}{\beta^\alpha \Gamma(\alpha)} t^{\alpha-1} e^{-t/\beta},$$

where R is the residue function and $\alpha$ and $\beta$ are two parameters.

In some embodiments, the non-linear observation model for the contrast agent concentration ($y_t$) over time may comprise a first (f) component and second component ($\varepsilon$), the first term representing the product of the blood flow, preferably the cerebral blood flow (CBF) or other body parts, and the tissue concentration ($C_a$) folded with the residue function, and the second term representing the observation error thereof ($\varepsilon_t$), respectively, cf. equation (2.3) below, this separation facilitating improved modelling. In one variant, the non-linear observation model for the contrast agent concentration ($y_t$) over time may further comprise a third term representing a leakage component of contrast agent over time from vascular to extravascular and extracellular space, if physiologically relevant for the mammal and/or potential disease being investigated.

In particular the ability to obtain robust estimates of perfusion modalities which are unaffected by tracer extravasation (leakage) is necessary in pathological conditions such as tumors, cerebral edema and multiple sclerosis where the blood-brain-barrier may be disrupted. Failing to model the loss of tracer to surrounding tissue will otherwise result in biased perfusion quantification.

Particularly, the non-linear observation model may have the form:

$$yt = f(C_a(t), \theta) + \in_t$$

$$\theta = \eta_\theta + \in_\theta$$

where $\theta$ is an unknown parameter being a function of the blood flow, preferably the cerebral blood flow (CBF), the parameters ($\alpha$, $\beta$) of the parametric model, and a time delay ($\delta$) representative of the delay between the site of measurement of $C_a$ and the site of measurement of $y_t$. The delay can be estimated, calculated, and/or predicted, for example based on previous data for the specific mammal, e.g. patient, and/or based on data obtained from populations of more subjects having the same, a similar or a related disease. The present invention has been demonstrated to be particularly advantageous for incorporating the effects of this delay, cf. FIG. 4A and corresponding description below.

Beneficially, a linearization of the non-linear observation model may be performed according to:

$$f(C_a(t), \theta) \approx \tilde{f}(\theta) = f(\hat{\theta}^{(i)}) + J(\theta - \hat{\theta}^{(i)})$$

where $$J = \frac{\partial}{\partial \theta} f(\hat{\theta}^{(i)}).$$

Furthermore, residual, r, may be defined as $$r = y - f(\hat{\theta}^{(i)}) + J\hat{\theta}^{(i)},$$

where y again denotes the contrast agent concentration curve, and where $$r = J\theta + \in$$

$$\theta = \eta_\theta + \in_\theta$$

so that the distribution of y may be defined as a statistical linear model, which may facilitate easier subsequent modelling as explained below.

Advantageously, one or more parameters of the statistical linear model may then be estimated using the minorize-maximize (MM) type procedure, preferably the expectation-maximization (EM) type procedure, to optimize a function related to perfusion, such as a likelihood function or posterior probability. Beneficially, the said function may be the posterior probability and the convergence of the minorize-maximize (MM) type procedure, preferably the expectation-maximization type procedure, may be monitored so as to assess the choice of prior distributions of parameters of the statistical linear model, where specifically the prior mean values of the parameters are updated when convergence of the algorithm to a non-optimal stationary state is obtained. This procedure is also denoted re-initialization of prior parameters Beneficially, the minorization may be obtained using the expected value of a function, preferably a joint loglikelihood function, more preferably by using the expectation maximization (EM) type procedure:

$$E\text{-step: } Q(C_\epsilon) = \mathbb{E}_{q(\theta|y)} \ln p(\theta, y) | C_\epsilon)$$

$$M\text{-step: } \underset{C_\epsilon}{\arg\max} Q(C_\epsilon)$$

In a particular preferred embodiment, the variance of an observation error of the contrast agent ($C_\epsilon$) may functional dependent at least on J, $C_{0\theta|y}$, and the residual r, which may be applied for improved estimation of perfusion indices.

More beneficially, the variance of an observation error of the contrast agent ($C_\epsilon$), under the assumption that $C_\epsilon = \sigma^2 I$, can be written:

$$\sigma^2 N = tr(JC_{\theta|y}J') + (r - Jn_{\theta|y})'(r - Jn_{\theta|y}),$$

where N is the number of contrast agent concentration measurements, resulting in an exact analytical expression for the observation, which has significant impact on the speed and quality of the perfusion indices obtainable by the present invention. When more than one variance component is present, a Fischer scoring algorithm can be applied.

In some embodiments, the method may estimates a perfusion index indicative of the heterogeneity of the blood flow in a capillary bed of the mammal, such CTTH or CTH, which has recently been demonstrated to be of significant physiological importance. In other embodiments, the method may estimate a perfusion index indicative of an extraction capacity (EC) of a substance, preferably oxygen (OEC, OEF) and/or glucose or other biochemical substances, from the blood in a capillary bed of the mammal.

The invention may estimate one or more perfusion indices from the non-exhaustive group consisting of: mean transit time, (MTT), blood flow, preferably the cerebral blood flow (CBF), blood volume, preferably the cerebral blood volume (CBV), and leakage ($K_{trans}$ or K2).

A variant of the first aspect of the invention relates to providing a method for estimating perfusion indices in a mammal, the method comprising:
  obtaining data representative of a contrast agent concentration as a function of time of an injected contrast agent, and
  estimating perfusion indices by applying:
    a parametric model (PM) for capillary transit time distributions as a function of time, and
    a minorize-maximization (MM) type procedure, preferably an expectation-maximization (EM) type procedure, with regularization for estimating of the perfusion indices,
wherein the minorization-maximization type procedure, preferably the expectation-maximization type procedure, comprises an exact analytical expression for the variance of an observation error of the contrast agent ($C_\epsilon$) in a non-linear observation model for the contrast agent concentration used in the maximization step.

In a second aspect, the invention relates to a medical imaging system, the system comprising:
  an imaging modality for obtaining data representative of contrast agent kinetics of an injected contrast agent, and storage means for optionally storing said data, and
  a processor arranged for estimating perfusion indices according to the first aspect.

Any medical imaging system suitable for obtaining data representative for a contrast agent concentration in a capillary structure of mammal is contemplated for application within the general teaching and principle of the present invention.

The imaging modality may particularly be selected from the non-exhaustive group consisting of: nuclear magnetic resonance imaging (MRI), including DSC-MRI and DCE-MRI (cardiac MRI), positron emission tomography (PET), single photon emission computed tomography (SPECT), computed tomography (CT), ultrasonic methods, multiple-photon spectroscopic methods, including two-photon imaging, Orthogonal Polarization Spectral (OPS) imaging, Sidestream dark-field (SDF) imaging, confocal imaging, laser Doppler measurements, laser scanning optometry of retina, and capillaroscopy, and any combinations thereof.

In a third aspect, the invention relates to a computer program product being adapted to enable a computer system comprising at least one computer having data storage means in connection therewith to control an imaging modality and/or imaging medical system for estimating perfusion indices in an associated mammal according to the second aspect of the invention.

This aspect of the invention is particularly, but not exclusively, advantageous in that the present invention may be accomplished by a computer program product enabling a computer system to carry out the operations of the apparatus/system of the second aspect of the invention when down- or uploaded into the computer system. Such a computer program product may be provided on any kind of computer readable medium, or through a network.

The individual aspects of the present invention may each be combined with any of the other aspects. These and other aspects of the invention will be apparent from the following description with reference to the described embodiments.

BRIEF DESCRIPTION OF THE FIGURES

The method according to the invention will now be described in more detail with regard to the accompanying figures. The figures show one way of implementing the present invention and is not to be construed as being limiting to other possible embodiments falling within the scope of the attached claim set.

FIG. 1 is an illustration of the exact CTTH and $OEF^{max}$ maps of the digital phantom. Also shown are the corresponding computed maps for two levels of SNR. The unit of the color bar is seconds for the CTTH maps, while the $OEF^{max}$ maps are dimensionless.

FIG. 2 shows MTT maps computed by the proposed parametric, sSVD, and oSVD methods for SNR=20 and SNR=100. The map consisting of squares with correct MTT values is shown at the left.

DETAILED DESCRIPTION OF AN EMBODIMENT

Figure 8:
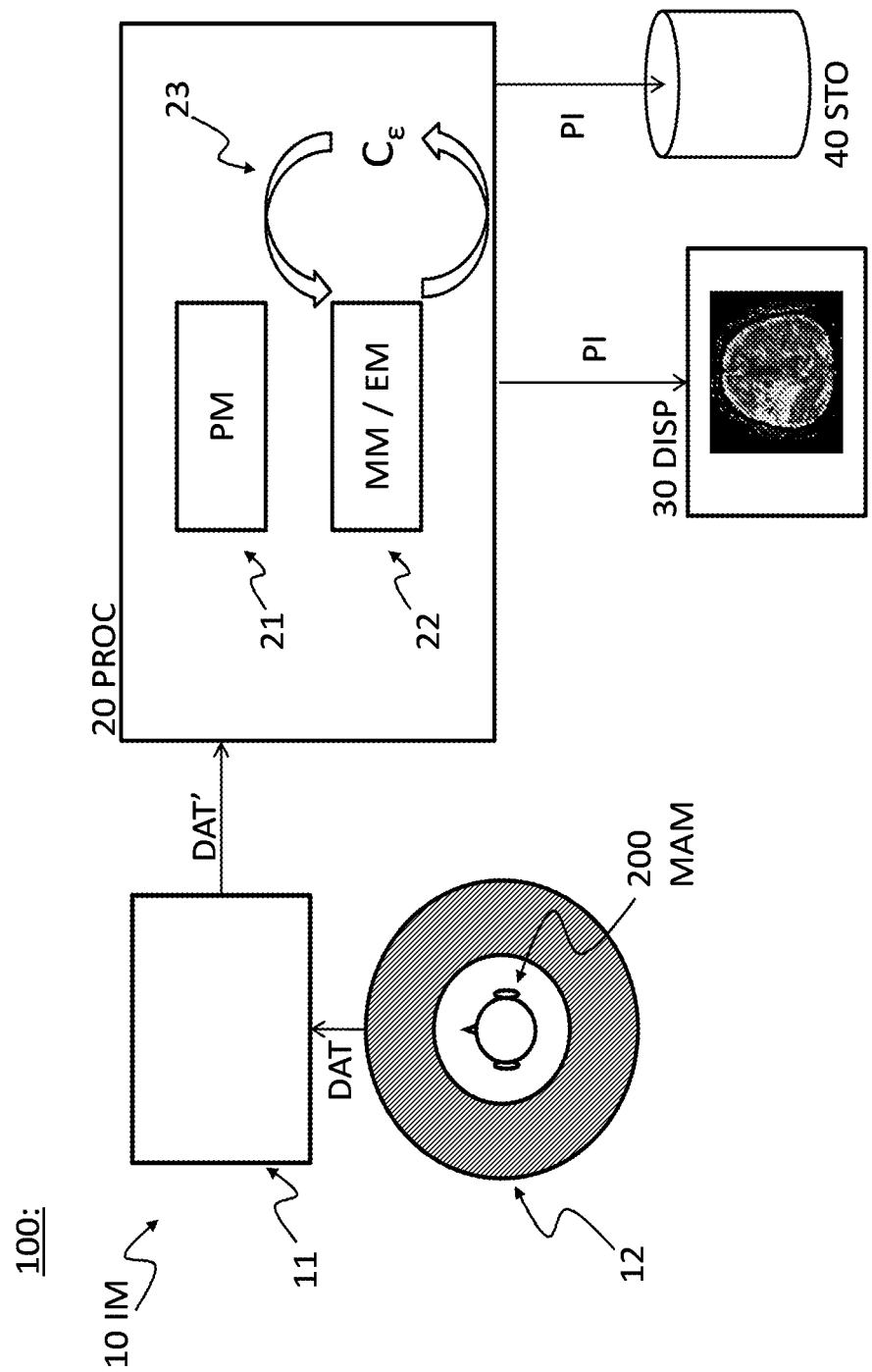
FIG. 8 is a schematic drawing of a medical imaging system 100 in a second aspect of the present invention.

FIG. 8 is a schematic drawing of a medical imaging system 100 in an aspect of the present invention. The system 100 comprises a medical imaging modality 10 IM, e.g. a DSC MRI modality as depicted here, capable of obtaining data representative of a contrast agent concentration as a function of time of an injected contrast agent into a mammal 200 MAM, e.g. a human being whose head is schematically seen in a cross-sectional view. One or more parts of the mammal can be imaged, e.g. the brain. The DSC MRI typically comprises a high magnetic MR scanner 12 and a corresponding measurement and control system 11. The scanner obtains primary data DAT which are communicated to the measurement and control system 11, where further processing resulting in secondary data DAT' being communicated to a processor 20 PROC.

In the processor 20 PROC, a method for estimating perfusion indices for the mammal 200 MAM is implemented using the obtained data DAT and DAT' representative of a contrast agent concentration as a function of time of an injected contrast agent. The perfusion indices are estimated by applying especially a parametric model PM 21 for the capillary transit time distributions as a function of time in a capillary structure, e.g. in a brain. Furthermore, a minorize-maximization MM procedure, preferably an expectation-maximization EM procedure 22 is used as will be explained in more detail below. There is also performed regularization when estimating the perfusion indices.

More particularly, the minorize-maximization MM procedure, preferably the expectation-maximization EM procedure, comprises an exact analytical expression for the variance of an observation error of the contrast agent $C_\varepsilon$ in a non-linear observation model for the contrast agent concentration used in the maximization step as schematically indicated by the arrows 23.

The processor may be operably connected to a display device 30 DISP, such as a computer screen or a monitor, so as to enable showing an image of the resulting perfusion indices PI as schematically indicated. Alternatively, or additionally, the perfusion indices PI may be communicated to a storage device 40 STO of any suitable kind for later analysis and for diagnostic purposes.

2. Theory 2.1. Tracer Kinetic Model

We assume that for a given tissue voxel, an intravascular tracer is delivered to the capillary bed with a characteristic arterial blood concentration denoted $C_a(t)$ where t denotes time. Using indicator-dilution theory, the concentration of tracer in the capillaries at time t is proportional to the convolution of the arterial supply with the residue function R(t), which represents the fraction of tracer still present in the capillaries at time t;

$$\kappa C(t) = CBF \int_0^t C_a(t-\tau) R(\tau) d\tau \quad (2.1)$$

The constant $\kappa$ depends on microvascular hematocrit levels in the arteriole and capillaries and the density of brain tissue, but is assumed constant in this embodiment.

We adopt a gamma distribution for the capillary transit times to enable parametric estimation of the residue function $$h(t \mid \alpha, \beta) = -\frac{dR}{dt} = \frac{1}{\beta^\alpha \Gamma(\alpha)} t^{\alpha-1} e^{-t/\beta} \quad (2.2)$$

To accommodate any delay in tracer delivery to the capillaries relative to the site of AIF measurement, an additional parameter is included in the model in order to permit shifts in the AIF timing, i.e. $C_a(t) \rightarrow C_a(t-\delta)$.

2.2. Parameter Estimation

For measurements of the contrast concentration over time we assume the non-linear observation model $$y_t = f(C_a(t), \theta) + \in_t \quad (2.3)$$

$$\theta = \eta_\theta + \in_\theta \quad (2.4)$$

with f denoting the right hand side in (2.1) and $\theta$ representing the unknown parameter $\theta = (CBF, \alpha, \beta, \delta)$. We assume a zero-mean Gaussian distribution for the observation error $\varepsilon$ with covariance $C_\varepsilon$. The parameter vector is also assumed to be stochastic with mean $\eta_0$ and covariance matrix $C_\theta$. Parameter estimation can be performed from a frequentist point of view using the marginal distribution p(y) of $y = (y_1, \ldots, y_N)$. It is natural to estimate the free parameters using an expectation-maximization (EM) algorithm, due to the unobserved stochastic elements in (2.4), cf. Dempster et al. (1977). In the following we employ an EM-type algorithm based on a commonly applied linear expansion around a current estimate of the random effect, which still permits prior distributions on e, cf. Mouridsen et al. (2006). In contrast to previous methods, the present invention applies an explicit equation for exact maximization in the M-step. A detailed description is provided in Appendix A.

To linearize the model we consider the first order expansion of f about a current estimate $\hat{\theta}^{(i)}$ of the random effect (2.3), (2.4)

$$f(C_a, \theta) \approx \tilde{f}(\theta) = f(\hat{\theta}^{(i)}) + (\theta - \hat{\theta}^{(i)}) \quad (2.5)$$

where $$J = \frac{\partial f(C_a, \theta)}{\partial \theta}\bigg|_{\theta=\hat{\theta}(i)}$$

For the residual $$\gamma = y - f(\hat{\theta}^{(i)}) + J\hat{\theta}^{(i)},$$

where y denotes the tissue concentration curve, we have $$r = J\theta + \epsilon \quad \epsilon \sim N(0, C_\epsilon)$$

$$\theta = \eta_\theta + \epsilon \quad \epsilon_\theta \sim N(0, C_\theta)$$

The marginal distribution of the data is $$p(r) = N(J\eta_\theta, C_\epsilon + JC_\theta J'), \quad (2.6)$$

assuming that $\epsilon$ and $\epsilon_\theta$ are independent on each other. Effectively this is a special case of a statistical linear mixed model, where the second term in the covariance structure in (2.6) results from the random effects. However, to allow regularization of parameter estimates we use a Bayesian approach where the hyper-parameters $N(\eta_\theta, C_\theta)$ of $\theta$ are given, N being the normal distribution. In the implementation they will be determined by a model free approach, see Section 3.2. An EM-type algorithm naturally applies to estimating the error covariance C and the posterior mean $\eta_{\theta|y}$ and covariance $C_{\theta|y}$ of $\theta$.

$$\mathbb{E}_{q(\theta|y)} \ln p(\theta, y \mid C_\epsilon) = \quad (2.11)$$

$$-\frac{1}{2}\ln|C_\theta| - \frac{1}{2}tr(C_\theta^{-1} C_{\theta|y}) - \frac{1}{2}(\eta_{\theta|y} - \eta_\theta)' C_\theta^{-1}(\eta_{\theta|y} - \eta_\theta) -$$

$$\frac{1}{2}\ln|C_\epsilon| - \frac{1}{2}tr(C_\epsilon^{-1} J C_{\theta|y} J') - \frac{1}{2}(r - J\eta_{\theta|y})' C_\epsilon^{-1}(r - J\eta_{\theta|y})$$

The mean in the E-step is taken with respect to $q(\theta|y)$, which is the Gaussian posterior density of $\theta$ given the observations y. The posterior moments of $\theta$ are $$C_{\theta|y} = (C_\theta^- + J'C_\epsilon^{-1} J)^{-1} \quad (2.9)$$

$$\eta_{\theta|y} = C_{\theta|y}(J'C_\epsilon^{-1} r + C_\theta^{-1} \eta_\theta) \quad (2.10)$$

The expression to be maximized in the M-step is $$E\text{-step: } Q(C_\epsilon) = \mathbb{E}_{q(\theta|y)} \ln p(\theta, y \mid C_\epsilon) \quad (2.7)$$

$$M\text{-step: } \underset{C_\epsilon}{\operatorname{argmax}} Q(C_\epsilon) \quad (2.8)$$

Since only a single voxel is analyzed at a time, a simple form of the error covariance $C_\epsilon$ must be assumed to ensure identifiability of the parameters, and we consequently consider $C_\epsilon = \sigma 2 I$. We show in Appendix A that the M-step can be performed analytically such that the estimate of the variance component is $$\sigma^2 N = tr(J C_{\theta|y} J') + (r - J\eta_{\theta|y})'(r - J\eta_{\theta|y}) \quad (2.12)$$

where N is here the number of observations.

As in Mouridsen et al. (2006) the expansion point is reset using regularization with a Levenberg-Marquardt damping factor, by taking advantage of the equivalence of the EM-approach to estimating the posterior modes with a Newton algorithm maximizing the posterior density of $\theta$.

3. Materials and Methods 3.1. Calculating Oxygen Extraction Capacity

The relations between capillary transit times and maximum oxygen extraction fraction, $OEF^{max}$ are described in more detail in Jespersen and ⌊stergaard (2012). $OEF^{max}$ is defined as $$OEF^{max} = \int_0^\infty h(\tau|\alpha,\beta) Q(\tau) d\tau \quad (3.1)$$

where $h(\tau)$ is the capillary transit time distribution (2.2) and Q is the oxygen extraction along a single capillary with transit time $\tau$. Q is obtained as the numerical solution to the ordinary differential equation (see Jespersen and ⌊stergaard (2012) for details).

$$\frac{dC}{dx} = -kr\left(\alpha_H P_{50}\left(\frac{C}{B-C}\right)^{\frac{1}{k}} - \alpha_H C_t\right) \quad (3.2)$$

here k describes the capillary wall permeability to oxygen, C is the concentration of oxygen, and $\tau$ is the capillary transit time. The remaining constants have been adopted from Jespersen and ⌊stergaard (2012), and are $\alpha_H = 3.1 \times 10^{-5}$ mmHg$^{-1}$, B=0.1943 mL/mL, $P_{50}$=26 mmHg, and $C_t$=25 mmHg. The rate constant k is set by requiring $OEF^{max}$=30% in normal-appearing white matter in the clinical stroke data included in this paper, see section 3.5. The resulting value is found to be k=38 s$^{-1}$.

3.2. Specifying the Prior Mean and Covariance

Computationally efficient estimates of CBF and MTT can be obtained using singular value decomposition (SVD). Although these estimates are known to be biased, Mouridsen et al. (2006), they may provide feasible first approximations, and are therefore used to center the prior in this embodiment. Delay is estimated as the time Tmax to the maximum of the non-parametric estimate of the residue function. Assuming for the prior that the residue function is exponential, we set $\alpha=1$ in (2.2) which implies $\beta$=MTT.

Acknowledging the inaccuracy of non-parametric estimates, the quality of the fit using the estimates of the EM-algorithm is monitored by a relative root mean square error measure, i.e.

$$\epsilon_{thr} = \left(\frac{\sum_i (y_i - \hat{y}_i)^2}{\sum_i y_i^2}\right)^{\frac{1}{2}} \quad (3.3)$$

where $y_i$ represents data point i, and $\hat{y}_i$ the corresponding estimated value. If the squared error criterion exceeds a preset value for the final EM-estimates (e.g. $\epsilon_{thr}$>0.03), we reset the prior mean of CBF and $\delta$ to the current estimates while a is set to $\alpha$=1 and 9=MTT. The EM procedure is then repeated. This approach works well here although we forego direct optimization of $\epsilon_{thr}$.

For the prior covariance of the parameters, i.e. $C_\theta$, we use a diagonal matrix, which reflects typical relative magnitudes of the corresponding parameters. Specifically, we set $C_\theta$=diag(0.1, 1, 1, 10). As in Mouridsen et al. (2006) we model parameters on a log-scale, and the variances in $C_\theta$ therefore apply to the log-transformed parameters. We examine robustness to misspecification of $C_\theta$ in section 3.4.

3.3. Simulations

Signal intensity curves were generated as in Mouridsen et al. (2006) using (2.1) and assuming a linear relation between the contrast concentration and the transverse relaxation rate $R_{*2}$. Specifically, the AIF was simulated using a gamma-variate function, $$C_a(t) = \begin{cases} 0 & t \leq t_0 \\ a(t-t_0)^b e^{-(t-t_0)/c} & t > t_0 \end{cases} \quad (3.4)$$

with a=1, $t_0$=10, b=3 and c=1.5 to generate an arterial concentration time curve with a shape and amplitude typical of standard clinical injection schemes, Mouridsen et al. (2006). Simulations were performed for CBV=4%. Signal curves were then generated using $$S(t) = S(0)e^{-\kappa r_2 T_E C(t)} \quad (3.5)$$

with S(0)=100 and $T_E$=50 ms and where $r_2$ is the transverse relaxivity. In Eq. (3.5), we have assumed a linear relation between intravascular concentration of the agent and transverse relaxation rate. The constant $\kappa r_2$ was calibrated as in Mouridsen et al. (2006), to produce signal drops typically observed in DSC data, such that a CBF of 60 ml/100 g/min and a CBV of 4% produces a 40% signal drop relative to the baseline as is typical for normal gray matter. For the AIF $\kappa r_2$ was fixed to produce a 60% signal drop relative to baseline.

Gaussian noise with zero mean was added to the signal curves (3.5) to produce specific baseline SNRs, see section 3.4. The sampling rate was fixed at TR=1.5 s and an acquisition time of 99 s including a 10.5 s baseline was simulated.

3.4. Digital Phantom Images

The capillary transit time distribution h(τ) in Eq. (3.1) is completely specified by its mean, MTT=αβ and standard deviation CTH=β√α. To assess whether MTT and CTH can be independently estimated we created a digital phantom where these quantities vary on a grid. This mimics FIG. 4A in Jespersen and ⌊stergaard (2012) which illustrates the dependence of $OEF^{max}$ on the transit time distribution, although in the present study we consider a broader range of MTT and CTH values. Each phantom consists of 7×7 squares, all of which correspond to a certain combination of MTT and CTH. Each square is subdivided into 14×14 voxels, all with identical MTT and CTH, but different noise realizations. MTT varied from 2 s to 20 s along the x-direction and CTH from 2 s to 20 s along the y-direction. Squares were separated by two voxels. The true values of CTH and $OEF^{max}$ are shown in the left column in FIG. 1 'Exact', and the true MTT values are displayed in the left column in FIG. 2 'Exact'.

Phantoms were generated with SNRs between 10 and 500. Additionally, we simulated arterial tracer arrival delays by introducing a time difference between the start of the AIF and the start of the tissue curves C(t). Delays were varied between 0 s and 10 s. Dispersion during transport from site of measurement of the AIF to the observed concentration was simulated by fixing the shape parameter in the AIF (3.4) at b=3.0 while varying the rate parameter (c), to obtain values of the full width at half maximum (FWHM) ranging from 1 s to 6 s.

While the non-parametric SVD provides adequate initial estimates of hemodynamic parameters to serve as centers of the prior distribution, the prior covariance is more difficult to determine. We examine the robustness to misspecification by varying the scales of CBF and the transport function parameter α, which together represent overall flow (CBF) and transit time distribution (α). We consider an alternative covariance matrix $\tilde{C}_\theta$, where the variance of CBF has been scaled up by a factor of 10 and the variance of a has been scaled down by the same factor. This effectively interchanges the scales of CBF and a. We also evaluate algorithm performance in the digital phantom for covariance matrices with intermediate scale changes using as prior covariance matrix $$C'_\theta = (1-\zeta)C_\theta + \zeta \tilde{C}_\theta \quad (3.6)$$

and calculate the mean square error in the phantom for values of ζ ranging from ζ=0 to ζ=1 with increments of 1/20. We compare results of the present algorithm with exact maximization (2.12) to the iterative Fisher Scoring scheme in Mouridsen et al. (2006).

3.5. Patient Data

MRI from seven patients with anterior circulation strokes were included to compare the performance of the proposed algorithm with that of the standard SVD methods. Data were obtained as part of the I-Know stroke imaging project. The protocol was approved by relevant national ethics committees and informed consent was obtained prior to patient enrollment. Standard DSC-MRI was performed on a GE Signa Excite 1.5, GE Signa Excite 3, GE Signa HDx 1.5, Siemens Tri-oTim 3, Siemens Avanto 1.5, Siemens Sonata 1.5, Philips Gyroscan NT 1.5, or a Philips Intera 1.5. Dynamic echo planar imaging (TE 30/50 ms for 3/1.5 Tesla field strength, TR 1500 ms, FOV 24 cm, matrix 128×128, slice thickness 5 mm) was performed during intravenous injection of Gadolinium based contrast (0.1 mmol/kg) at rate of 5 ml/s, followed by 30 ml of physiological saline injected at the same rate. Follow-up fluid-attenuated-inversion-recovery (FLAIR) images were acquired after 1 week or one month to permit identification of the final infarct extent.

3.6. Image Processing

Analysis of phantom images as well as patient data was performed with in-house developed perfusion analysis software called 'Penguin' (comprising tools for AIF selection, parametric- and non-parametric deconvolution and image display). The software was developed at Center of Functionally Integrative Neuroscience (CFIN) institution at Aarhus University. In the clinical data, an arterial input function was identified semi-automatically by an expert radiologist. Parametric estimation of hemodynamic modalities was performed with the presets described in section 3.2. Standard SVD was applied with a threshold of 0.2, and with oSVD the oscillation index was set to 0.095. With the SVD methods delay was estimated as the time to maximum of the residue function (Tmax).

4. Results 4.1. Estimation of CTH and $OEF^{max}$ at specific SNRs

Figure 1A:
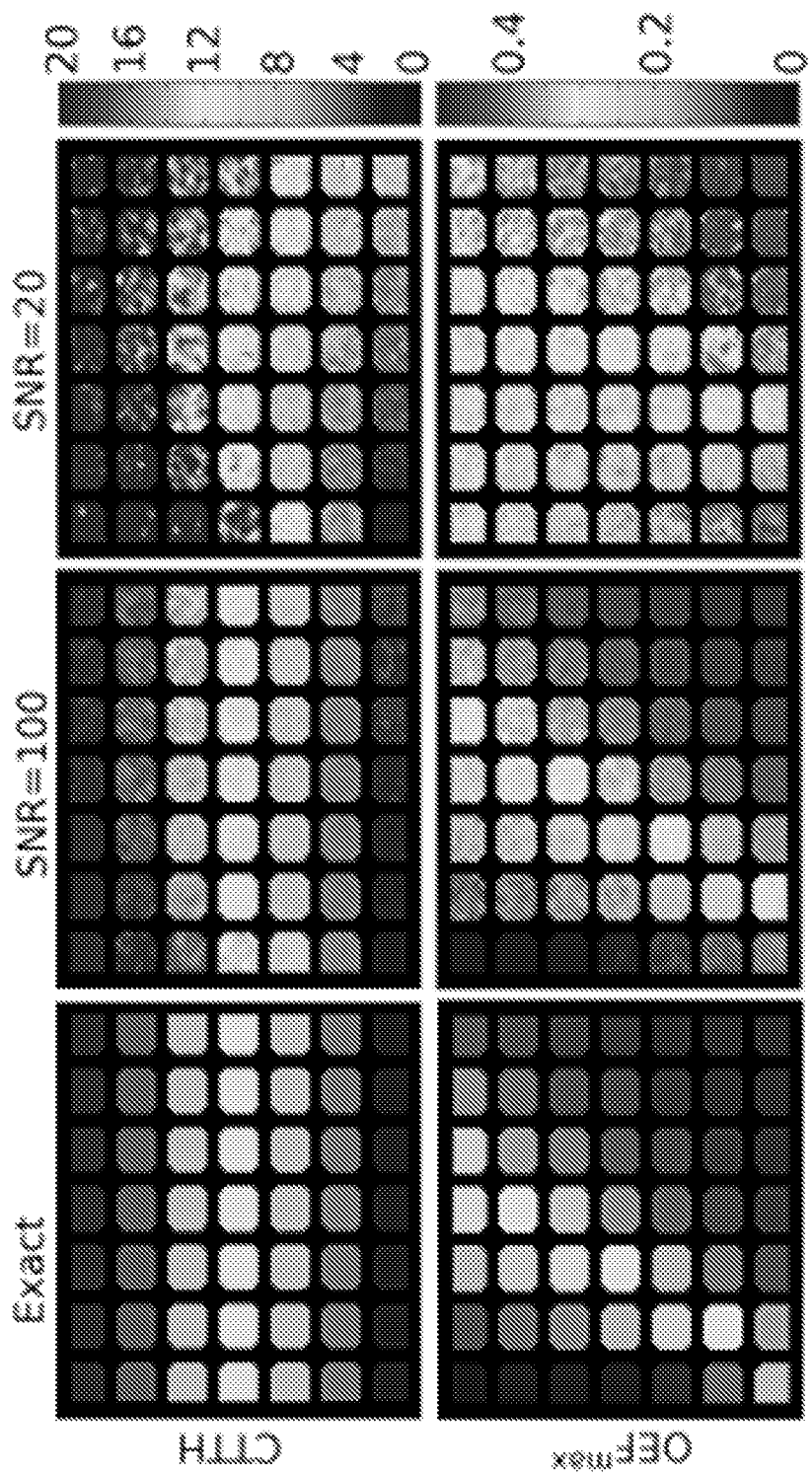
FIG. 1A is a colour version and FIG. 1B is the corresponding grey tone version.
Figure 1B:
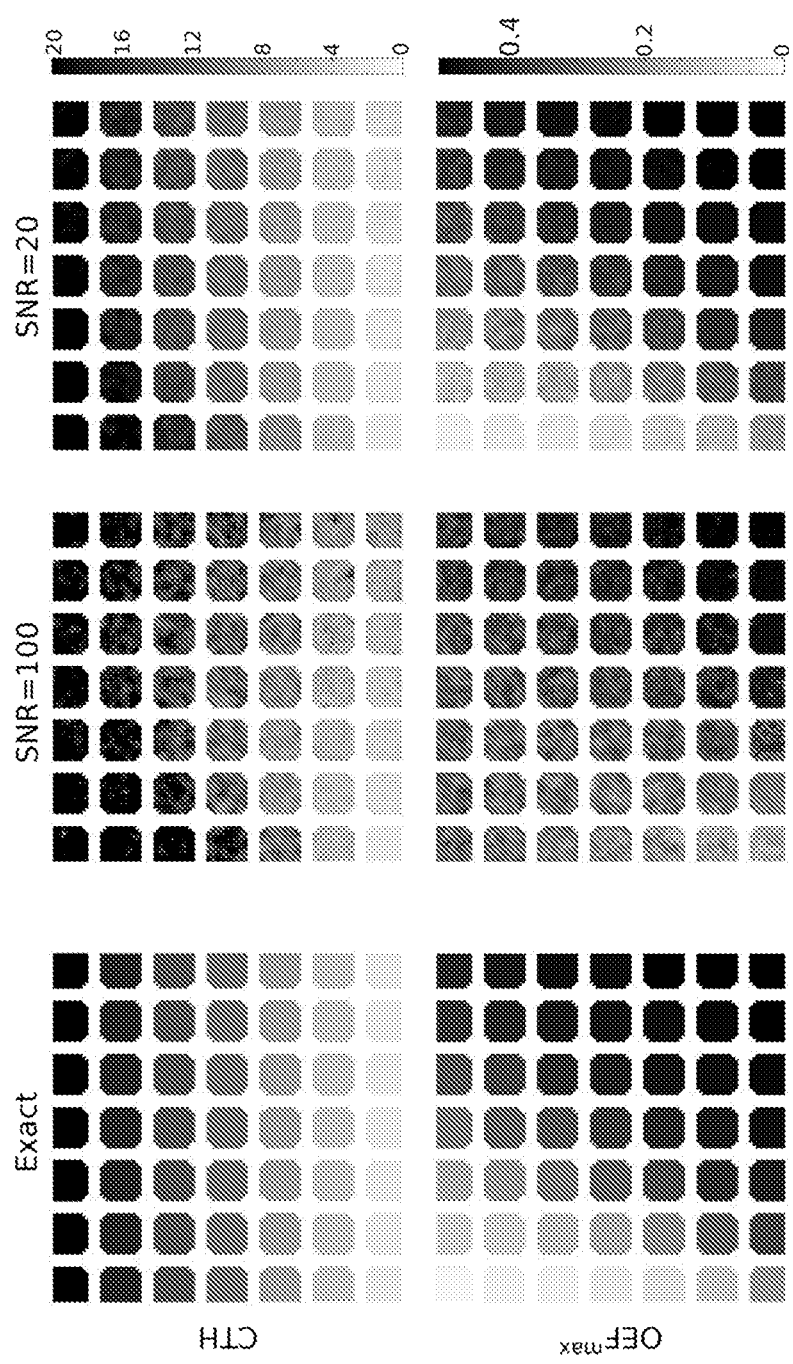

FIG. 1 shows $OEF^{max}$ and CTH estimates in the digital phantom at SNR=100 and SNR=20. The true values are displayed in phantom in the left column. At SNR=100 (center column), estimates of CTTH, or CTH, and $OEF^{max}$ are in good agreement with the true values, demonstrating no appreciable bias and little within-field intensity variation.

At SNR=20 the CTH estimates show low bias and little variation among squares in the horizontal direction, indicating that CTH can be estimated independently of MTT even in high-noise conditions. As expected, within-square variance increase at the lower SNR, but CTH differences remain discernible across MTT levels. As shown by the lower panels, the variance and bias of the $OEF^{max}$ estimates behaved in a similar fashion, except for some bias (overestimation) of $OEF^{max}$ in cases of very high flow (low MTT) and high transit time heterogeneity.

Figure 3:
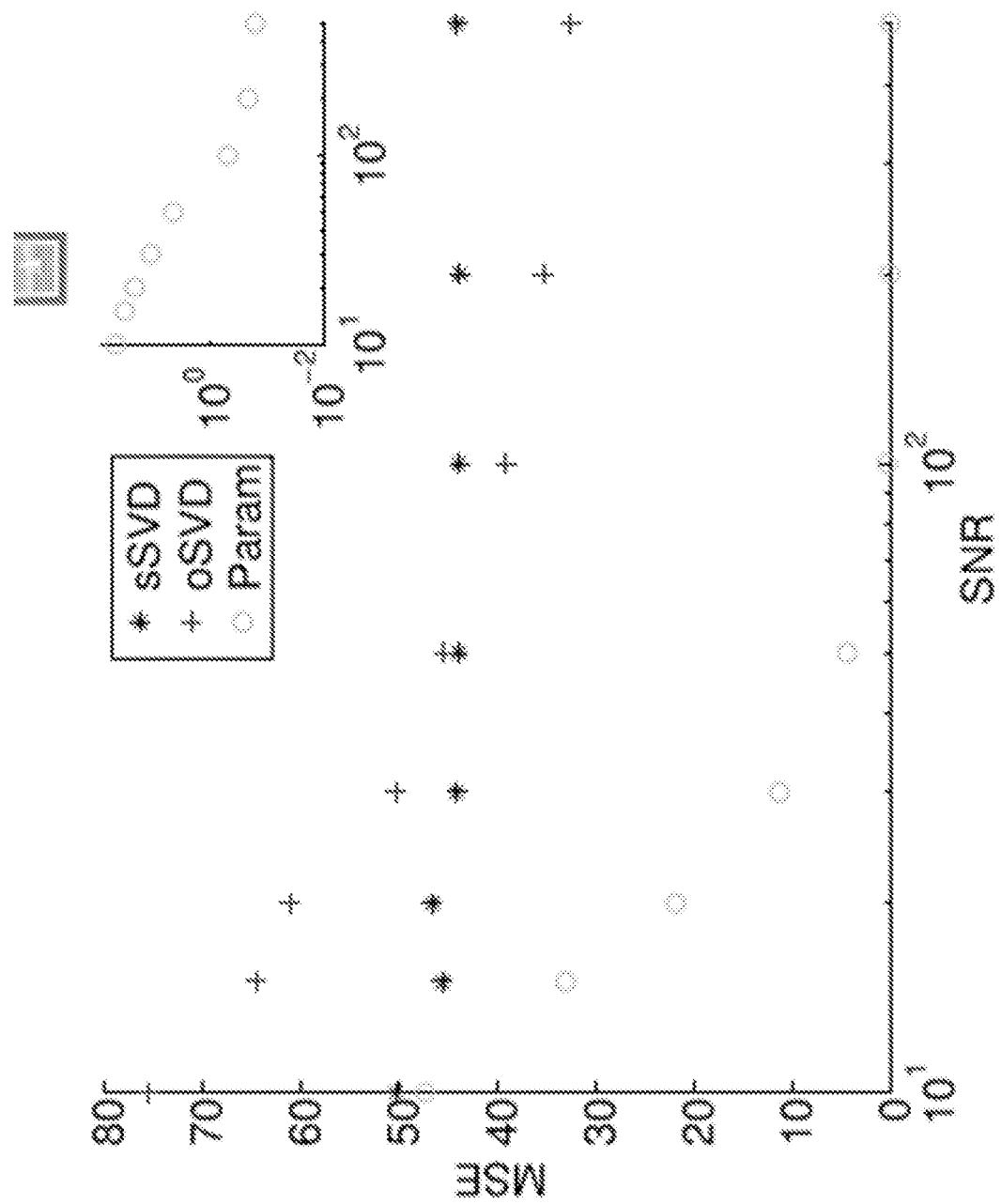
FIG. 3 is a graph showing mean squared error, MSE, of the MTT for the different models; sSVD, oSVD, and the parametric model (Param), as a function of the SNR, respectively. A maximum MTT value of 30 seconds has been enforced. The inset illustrates the convergence of the parametric model on a log-scale.

In FIG. 3, the relative mean square error (MSE) of the $OEF^{max}$ and CTH parameters is plotted for SNR in the range 10 to 500. Both parameters display fast convergence with respect to improvements in the SNR.

4.2. Estimation of MTT at Specific SNRs

Figure 2A:
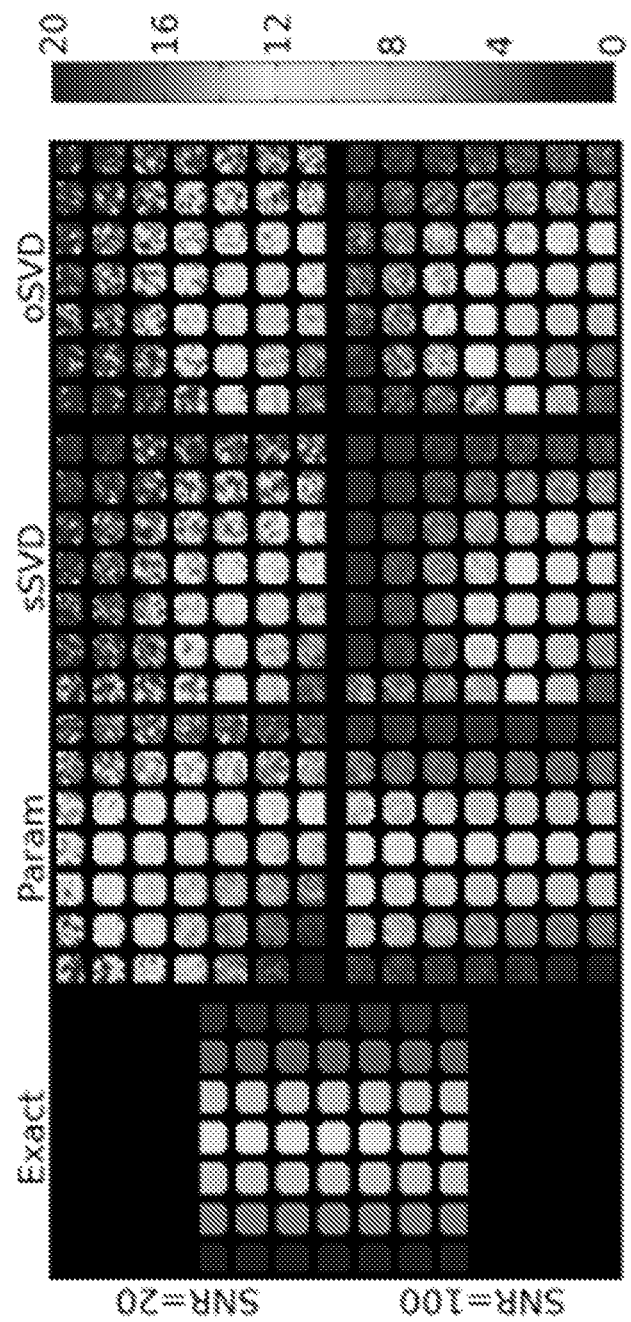
FIG. 2A is a colour version and FIG. 2B is the corresponding grey tone version.
Figure 2B:
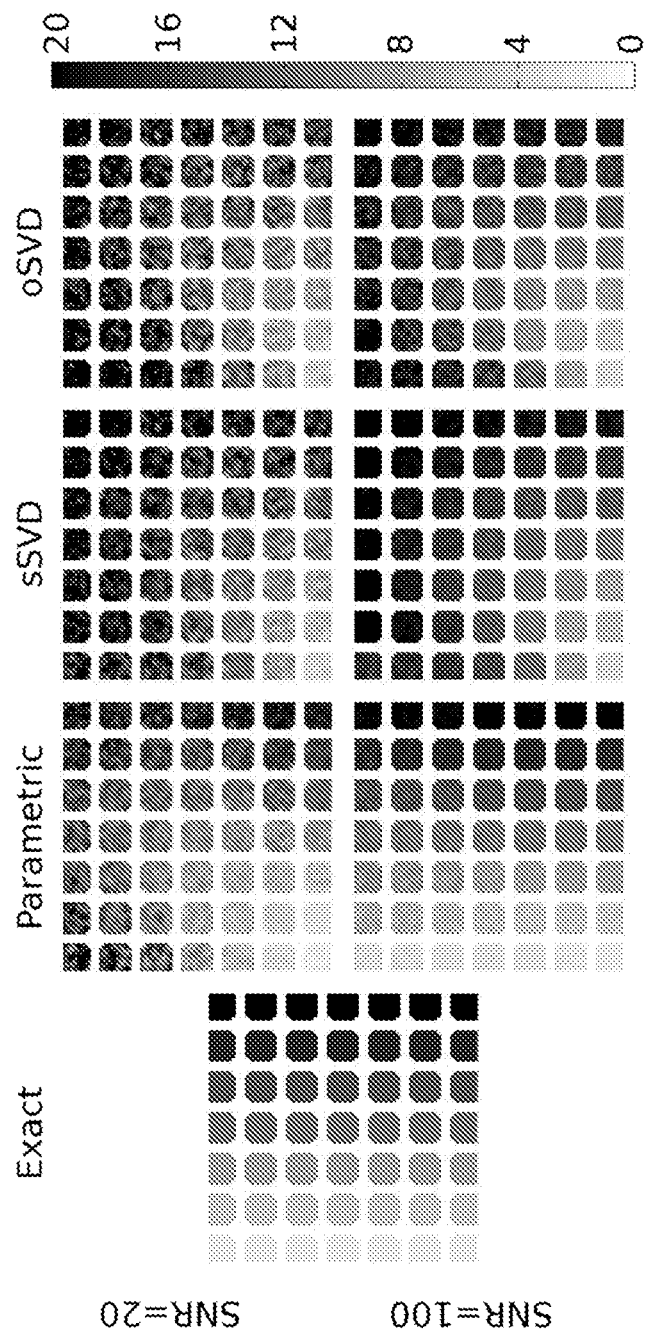

While CTH and $OEF^{max}$ estimates are specific to our technique, MTT estimates can be compared to sSVD and oSVD. FIG. 2 shows MTT estimates by the parametric model and by the two SVD techniques at SNR=100 (top panels) and SNR=20 (bottom panels). Comparing to the true MTT values shown to the far left we note that at SNR=100 the parametric model exhibits no discernible bias and exhibits low within-field variation. Combined with the similar results for CTH in FIG. 1 this ascertains the algorithm's ability to provide independent estimates of MTT and CTH. In comparison sSVD and oSVD both demonstrate substantial bias in MTT estimates. When CTH is low, as in the lower rows of the phantom, this bias is not pronounced, but it increases for moderate CTH (middle rows) and for high CTH, the MTT estimates appear close to uniform across columns.

At SNR=20 the parametric procedure demonstrates a slight bias in MTT for midrange values of CTH and for high CTH values this is more pronounced for low MTT values (upper left corner). The low MTT in this area implies the residue function must quickly drop from its maximum, while the simultaneously high CTH requires the residue function to remain non-zero over a long time period. Therefore the MTT overestimation in this region may be due to the low sampling rate, TR=1.5 s. The SVD methods display substantial bias even at very low CTH.

We note that along the diagonal from the lower left to the upper right corner the underlying residue function is exponential. Both SVD techniques appear to give reasonable estimates of MTT along this direction, which is consistent with previous published results.

4.3. General SNR Sensitivity

To compare the performance of the perfusion algorithms across a wider range of settings we summarize the concordance between the estimated and the true values by the RMSE. The results are shown in FIG. 3. The RMSE of the parametric algorithm rapidly decreases towards zero as SNR increases from 10 to 50. At SNR=50, the RMSE for the parametric algorithm is lower than for the SVD techniques by approximately a factor of 10. The RMSE for sSVD does not appear to improve with increasing SNR, whereas RMSE for oSVD decreases until SNR=50, but then only improves slightly as SNR increases further.

4.4. Sensitivity to Tracer Delay and Dispersion from Site of AIF Measurement FIG. 4A shows RMSE for all modalities, or perfusion indices PI, for tracer delays between 0 and 10 seconds, for fixed SNR=50.

Figure 4A:
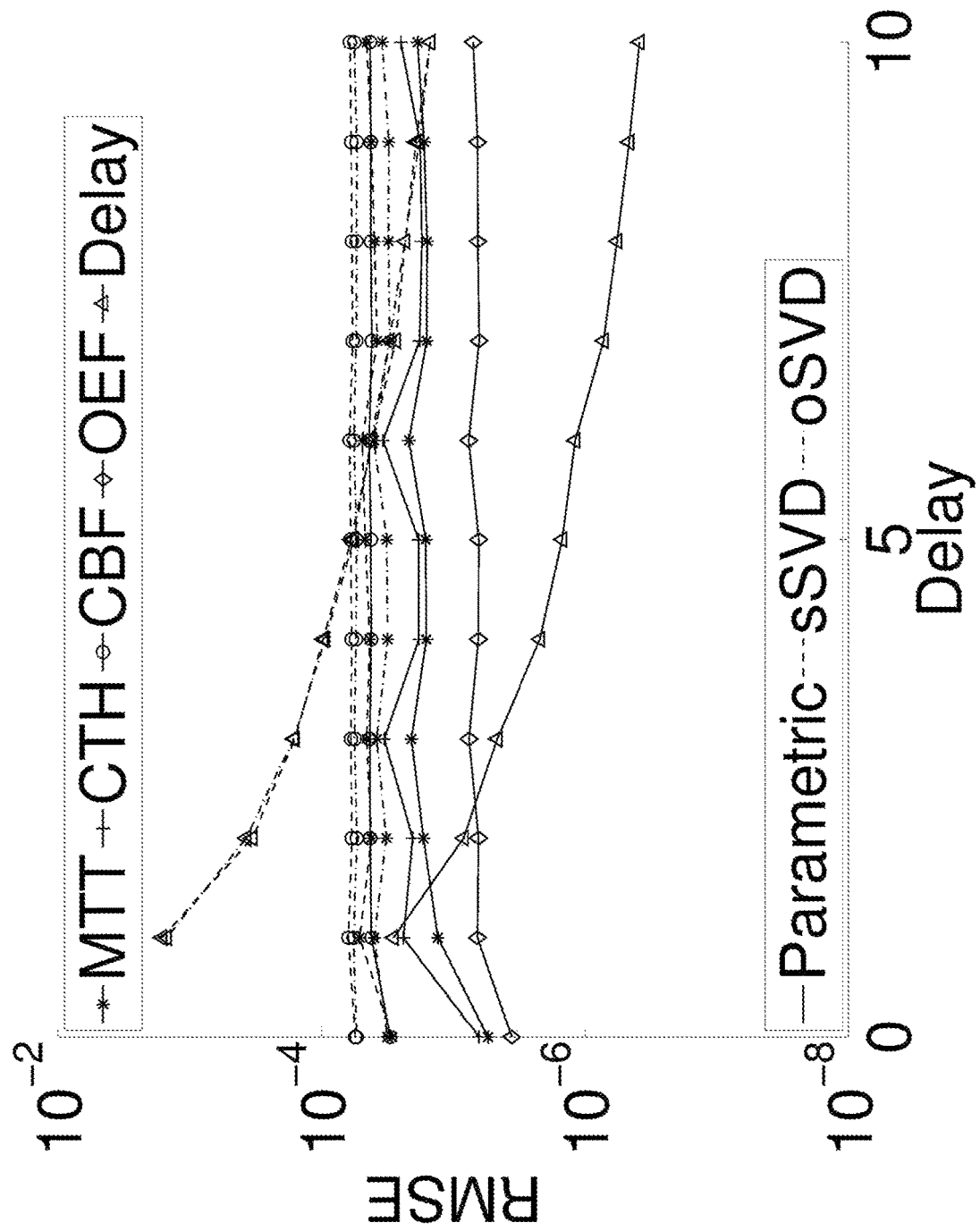
FIG. 4A is a graph showing RMSE as a function of delay using the parametric model (full lines) according to the present invention, and SVD (two kinds of dashed lines). The $OEF^{max}$ values are scaled by 1000, while CBF is a relative measure, see text. The delay is given in seconds.

In general, RMSE for the parametric maps exhibits little systematic dependence on delay (see FIG. 4A). The figure also confirms the delay insensitivity of oSVD CBF and MTT estimates, but we note that the RMSE for MTT is doubled in value relative to the parametric estimates, whereas CBF estimation errors are comparable between techniques. While very little estimation error is observed with the parametric approach, the error in oSVD delay estimates are quite constant for all values of delay sampled here. By inspection of the delay maps produced by the oSVD method (maps not shown here), there is a clear tendency for the delay to increase as MTT increases. This suggests an inability for oSVD to accurately separate MTT and delay.

Figure 4B:
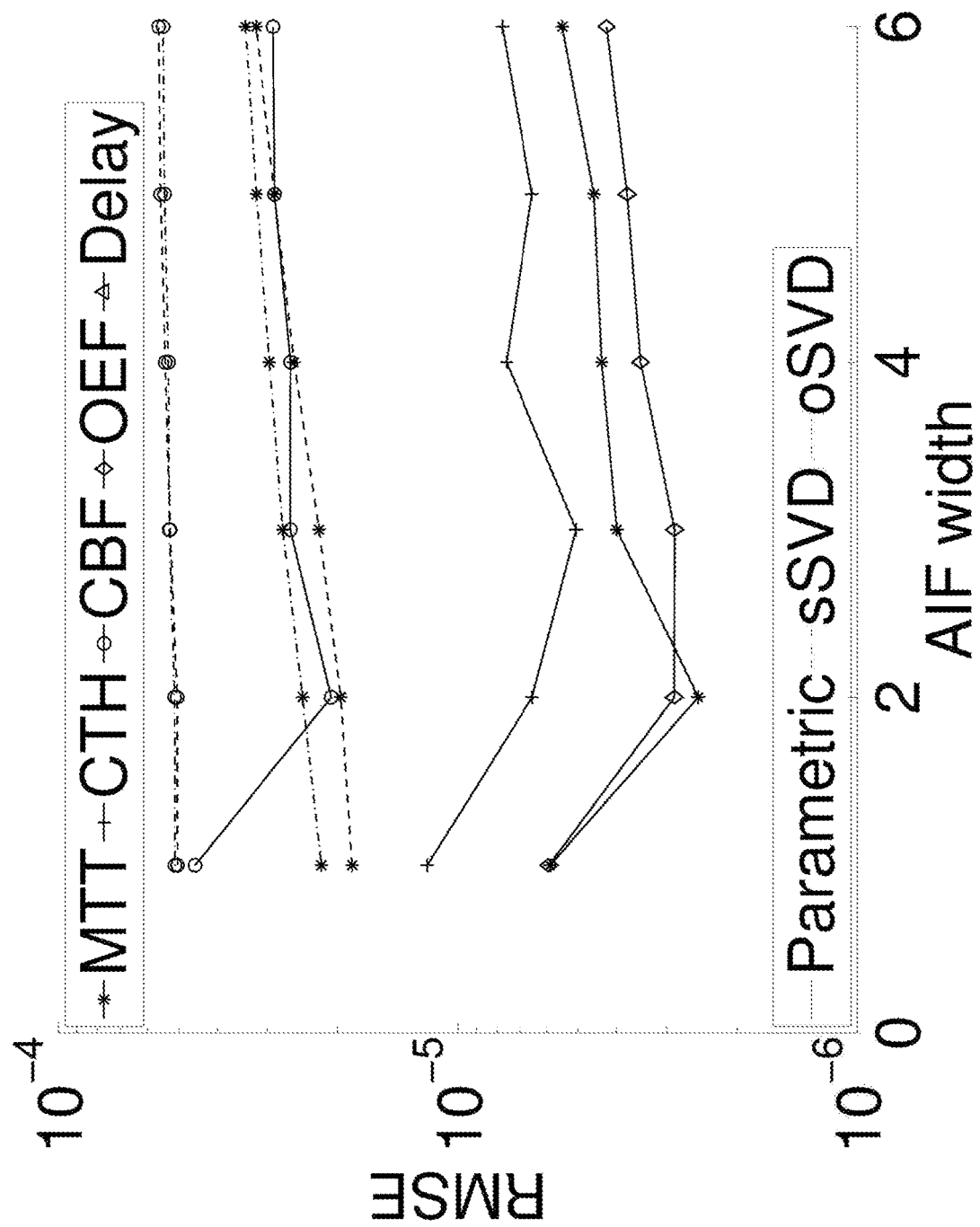
FIG. 4B is a graph showing MSE as a function of the FWHM ('width') of the AIF using the parametric (full lines) and SVD (two kind of dashed lines). The $OEF^{max}$ values are scaled by 1000, while CBF is a relative measure, see text. The FWHM is given in seconds.

FIG. 4B demonstrates that the maps produced by the parametric model are generally insensitive to moderate degrees of dispersion in the AIF, suggesting that perfusion estimates, or perfusion indices PI, can be estimated reliably in subjects 200 where vascular disease causes additional dispersion of the bolus prior to arrival in the brain. Similar results are observed for oSVD, except for a trend towards less accurate MTT estimation. We note that the large drop observed for the parametric model in going from one to two seconds, is likely related to the width of the AIF (FWHM) being lower than the sampling rate, which is fixed at TR=1.5 s. The oSVD method is not observed to display this feature.

4.5. Parametric Model: Robustness with Respect to Prior Covariance

Figure 5:
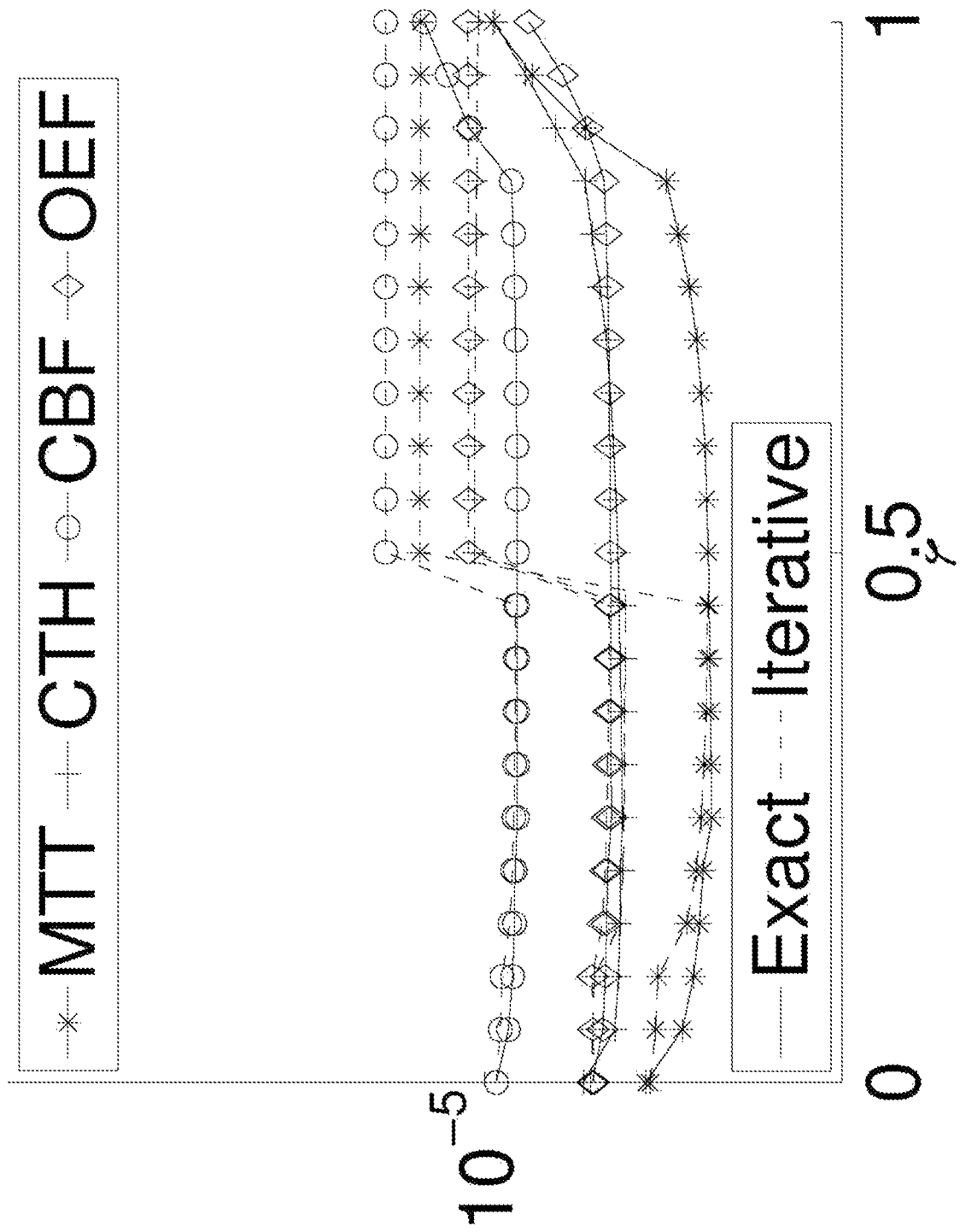
FIG. 5 is a graph showing the effect of scale changes in the prior covariance matrix. The exact maximization (full lines) according to the present invention provides robustness to scale changes whereas a sudden increase in MSE of perfusion estimates is observed with the iterative approach (dashed lines). Notice that $OEF^{max}$ values were scaled by 1000 for visual comparison in this graph.

In FIG. 5 $\zeta=0$ corresponds to the previously used prior covariance matrix and $\zeta=1$ represents a covariance matrix where the scales of CBF and a have changed by a factor of 10.

We see that the exact optimization approach is more robust to prior covariance misspecification than the iterative procedure, where a sudden increase in RMSE is observed across all modalities around $\zeta=0.5$.

4.6. Patient Data

Figure 6A:
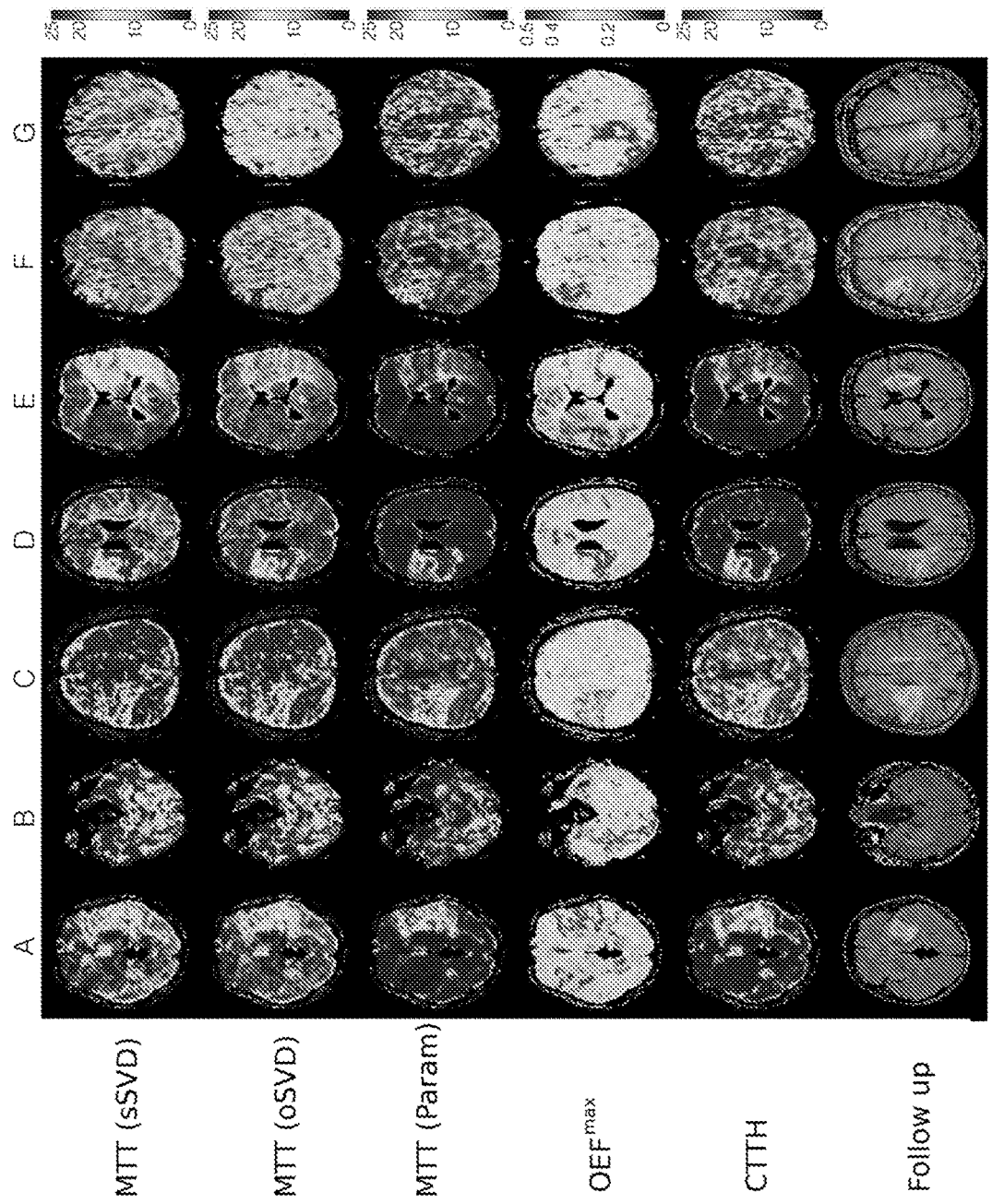
FIG. 6A shows perfusion markers for a set of clinically acquired stroke data. The color scales presented to the right pertain to all images in a row.
Figure 6B:
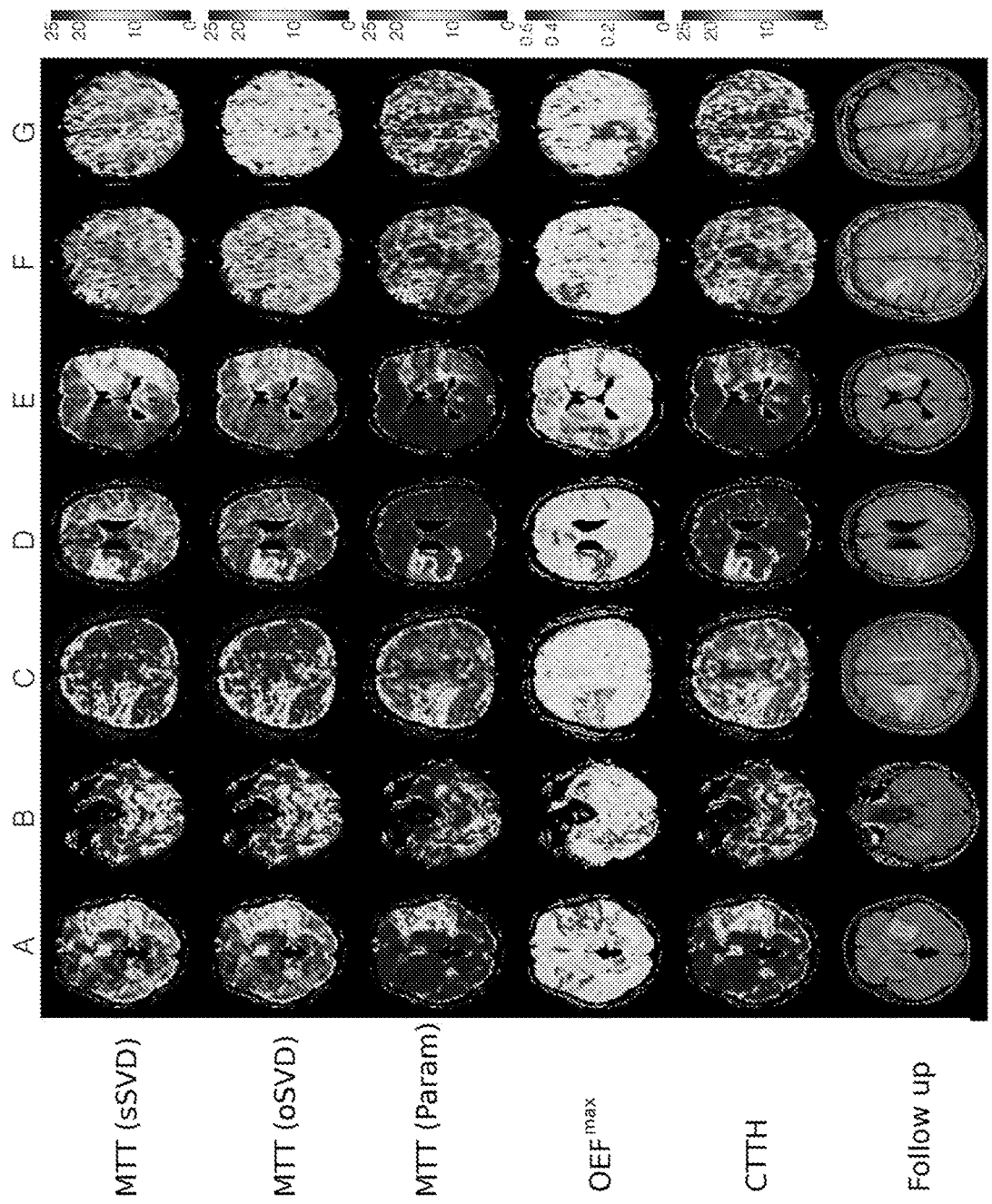
FIG. 6B is the corresponding grey scale version of the coloured FIG. 6A.

Clinical data for the seven stroke patients, labeled A-G, are presented in Table 1. FIG. 6 shows perfusion maps from the parametric procedure and the SVD techniques as well as follow-up FLAIR images showing the permanent lesion.

In patient A, all metrics demonstrate a large hypoperfused region consistent with the patient's neurological deficits (NIHSS=11), however parametric MTT and CTH images seem to distinguish the hypoperfused tissue more clearly from surrounding unaffected tissue. In patient B the lesion appears much less clear on SVD MTT, compared to parametric MIT, $OEF^{max}$ and CTH. Notably, the anterior boundary of the lesion is difficult to identify on SVD images due to image noise.

Scattered high-intensity regions are observed to an even greater degree in patient C, especially in the contralateral hemisphere, in the SVD maps. These areas appear hypoperfused in the SVD based images, but likely reflect artifacts generated by the deconvolution. This may be a consequence of low contrast-to-noise ratios (typically 3-5 in this patient) rendering portions of the concentration curve negative, and resulting in highly oscillating residue functions when directly fitted as with SVD. The parametric model may still be able to fit meaningful values from the shape of the bolus passage, and by construction, cannot become negative. This finding is consistent with our phantom simulations, in which low SNR gave rise to a significant overestimation of MIT for the SVD methods, see FIG. 2.

In patient D, there is less consistency in the lesion estimate across modalities, in particular with parametric MTT displaying a high-intensity volume consistent with the final outcome, whereas the SVD maps may suggest less grading of intensities. Since CTH appears elevated throughout the lesion it may be speculated, given the simulation results, that SVD MTT maps were confounded by transit time heterogeneity.

The apparent overestimation of perfusion lesions by SVD methods is more evi-dent in patient E, with parametric MTT only slightly elevated. A small perfusion lesion is consistent with the low NIHSS value. The parametric and SVD methods all indicate a large area of bolus delay, with an extend corresponding to the SVD MTT lesion (data not shown). This suggests neurological function was preserved due to efficient collateral supply in the MCA territory.

In contrast to patient E, patients F and G do not show any hypoperfusion on oSVD MTT, whereas lesions are clearly visible on parametric MTT, $OEF^{max}$ and CTH. The lesion is also visible on sSVD MTT for patient G, but much less in patient F. In both cases the lesions seen in the parametric images are consistent with the lesions seen on 1-month follow-up FLAIR. Inspection of the underlying signal curves revealed that short data acquisition time, resulting in truncated signal curves in hypoperfused tissues, may have contributed to this effect. The parametric model and standard SVD seemed unaffected by this phenomena in these cases.

5. Discussion

We have invented a statistical technique for estimating a novel hemodynamic quantity, CTH, and the derived oxygen extraction capacity, $OEF^{max}$ based on DSC-MRI. This method extends existing techniques for estimating the macroscopic tissue perfusion indices CBF, CBV, and MTT. Our simulation results demonstrate low bias and variance in CTH and $OEF^{max}$ estimates across a wide range of residue functions, even in data with poor SNR. Importantly, these estimates are also relatively insensitive to delay and dispersion artifacts, which are common concerns in acute stroke imaging.

We have demonstrated substantial improvements in MTT estimation compared to sSVD and oSVD. Notably, we have demonstrated that MTT estimates by the widely used sSVD and oSVD deconvolution algorithms are confounded by CTH (FIG. 2) even at low noise levels (SNR=100).

One major motivation for the present invention is to enable efficient estimation of novel markers of capillary flow distributions by means of a parametric model. In principle, non-parametric approaches such as sSVD and oSVD estimates the residue function, from which such parameters can be extracted in a second step. However, whereas model independent techniques estimate every time point of the unknown residue function, a model based approach estimates only the relevant perfusion quantities, resulting in more efficient and reliable estimation. The ill-posedness of the deconvolution problem (2.1) necessitates regularization, which for SVD techniques is implemented through various constraints on the oscillations in the residue functions. With the proposed parametric approach according to the present invention, regularization is facilitated through the prior expectation and variance of the perfusion parameters. Since these quantities can be obtained empirically from perfusion measurements, this may be a physiologically more appropriate approach to regularization.

Appendix A. Expectation Maximization

In this appendix we derive the exact expressions for the E- and M-step in the estimation algorithm in section 2 above. In the model $$r = J\theta + \epsilon \quad \epsilon \sim \mathcal{N}(0, C_\epsilon)$$

$$\theta = \eta_\theta + \epsilon_\theta \quad \epsilon_\theta \sim \mathcal{N}(0, C_\theta)$$

we consider $\eta_\theta$ and $C_\theta$ as fixed priors and estimate $C_\epsilon$, and use the posterior mean $\eta_{\theta|y}$ to reset the expansion point in Eq. (2.5).

The EM-algorithm first computes the expectation of the joint density of $\theta$ and $y$ with respect to a current estimate of the posterior density of $\theta|y$, and subsequently maximizes this expectation with respect to the unknown parameter $C_\epsilon$.

$$E\text{-step: } Q(C_\epsilon) = \mathbb{E}_{q(\theta|y)} \ln p(\theta, r \mid C_\epsilon) \quad (A.1)$$

$$M\text{-step: } \underset{C_\epsilon}{\arg\max}\, Q(C_\epsilon) \quad (A.2)$$

A.1. E-Step

The joint density $p(\theta, r|C_\epsilon)$ in Eq. (A.1) can be written as $$p(\theta, r|C_\epsilon) = p(r|\theta, C_\epsilon) p(\theta) \quad (A.3)$$

Since both densities are Gaussian we get $$\ln p(\theta, r \mid C_\epsilon) = \ln p(\theta) + \ln p(r \mid \theta)$$

$$= -\frac{1}{2}\ln|C_\theta| - \frac{1}{2}(\theta - \eta_\theta)' C_\theta^{-1}(\theta - \eta_\theta) - \frac{1}{2}\ln|C_\epsilon| -$$

$$\frac{1}{2}(r - J\theta)' C_\epsilon^{-1}(r - J\theta) + const$$

The posterior density of $\theta|y$ is also Gaussian with parameters $\eta_{\theta|y}$ and $C_{\theta|y}$ given in Eqs. (2.9) and (2.10). To calculate the mean of $\ln p(\theta, r|C_\epsilon)$ when $\theta$ has the posterior density $q$ we use that the expectation of the quadratic form $z'Az$ is $$\mathbb{E} z'Az = tr(A\Sigma) + \mu'A\mu \quad (A.4)$$

where A is a matrix, $Ez = \mu$ and $Cov(z) = \Sigma$. Therefore, since under the posterior distribution we have $$\theta - \eta_\theta \sim \mathcal{N}(\eta_{\theta|y} - \eta_\theta, C_{\theta|y})$$

it follows that $$\mathbb{E}_q (\theta - \eta_\theta)' C_\theta^{-1} (\theta - \eta_\theta) = tr(C_\theta^{-1} C_{\theta|y}) + (\eta_{\theta|y} - \eta_\theta)' C_\theta^{-1} (\eta_{\theta|y} - \eta_\theta)$$

Analogously $$r - J\theta \sim \mathcal{N}(r - J\eta_{\theta|y}, JC_{\theta|y}J')$$

to which gives $$\mathbb{E}_q (r - J\theta)' C_\epsilon^{-1} (\theta - J\theta) = tr(C_\epsilon^{-1} JC_{\theta|y} J') + (r - J\eta_{\theta|y})' C_\epsilon^{-1} (r - J\eta_{\theta|y})$$

Therefore the expression to be maximized with respect to C in the M-step is $$\mathbb{E}_q \ln p(\theta, r, C_\epsilon) = \quad (A.5)$$

$$-\frac{1}{2}\ln|C_\theta| - \frac{1}{2} tr(C_\theta^{-1} C_{\theta|y}) - \frac{1}{2}(\eta_{\theta|y} - \eta_\theta)' C_\theta^{-1} (\eta_{\theta|y} - \eta_\theta) -$$

$$\frac{1}{2}\ln|C_\epsilon| - \frac{1}{2} tr(C_\epsilon^{-1} JC_{\theta|y} J') - \frac{1}{2}(r - J\eta_{\theta|y})' C_\epsilon^{-1} \frac{1}{2}(r - J\eta_{\theta|y})$$

A.2. M-Step

To derive the exact optimization in the M-step we first let $C = \sigma^2 Q$, where Q describes the structure (e.g. weighting) of covariances, and calculate the partial derivative of (A.5). We note that $$\frac{\partial}{\partial \sigma^2} \ln|C_\epsilon| = tr\left(C_\epsilon^{-1} \frac{\partial}{\partial \sigma^2} C_\epsilon\right)$$

$$= tr(C_\epsilon^{-1} - Q)$$

$$\frac{\partial}{\partial \sigma^2} tr(C_\epsilon^{-1} JC_{\theta|y} J') = tr\left(\frac{\partial}{\partial \sigma^2}(C_\epsilon^{-1} JC_{\theta|y} J')\right)$$

$$= tr\left(\frac{\partial}{\partial \sigma^2}(C_\epsilon^{-1}) JC_{\theta|y} J'\right)$$

$$= tr((-C_\epsilon^{-1} QC_\epsilon^{-1})(JC_{\theta|y} J'))$$

-continued $$\frac{\partial}{\partial \sigma^2}(r-J\eta_{\theta|y})'C_\epsilon^{-1}(r-J\eta_{\theta|y}) = (r-J\eta_{\theta|y})'\frac{\partial}{\partial \sigma^2}(C_\epsilon^{-1})(r-J\eta_{\theta|y})$$
$$= -(r-J\eta_{\theta|y})'C_\epsilon^{-1}QC_\epsilon^{-1}(r-J\eta_{\theta|y})$$

The first derivative of the expression in the M-step can then be written as $$\frac{\partial}{\partial \sigma^2}\mathbb{E}_q\ln p(\theta,r\mid\sigma^2) = tr(C_\epsilon^{-1}Q) - tr((C_\epsilon^{-1}QC_\epsilon^{-1})(JC_{\theta|y}J')) - \quad (A.6)$$
$$(r-J\eta_{\theta|y})'C_\epsilon^{-1}QC_\epsilon^{-1}(r-J\eta_{\theta|y})$$
$$= tr(C_\epsilon^{-1}Q) - tr(C_\epsilon^{-1}JC_{\theta|y}J'C_\epsilon^{-1}Q) -$$
$$(r-J\eta_{\theta|y})'C_\epsilon^{-1}QC_\epsilon^{-1}(r-J\eta_{\theta|y})$$
$$= tr(PQ) - (r-J\eta_{\theta|y})'C_\epsilon^{-1}QC_\epsilon^{-1}(r-J\eta_{\theta|y})$$

where $$P = C_\epsilon^{-1} - C_\epsilon^{-1}JC_{\theta|y}J'C_\epsilon^{-1}$$

Now consider the case, where there is only a single variance component, i.e. $C=\sigma^2 I$. In this case, Eq. (A.6) reduces to $$\frac{\partial}{\partial \sigma^2}\mathbb{E}_{q(n)}\ln p(\theta,r\mid\sigma^2) = \sigma^{-2}N - \sigma^{-4}\{(r-J\eta_{\theta|y})'(r-J\eta_{\theta|y}) + tr(JC_{\theta|y}J')\}$$

where N is the number of observations. The optimal value can now be found directly by setting the differential equal to zero, yielding $$\sigma^2 N = tr(JC_{\theta|y}J') + (r-J\eta_{\theta|y})'(r-J\eta_{\theta|y})$$

End of Appendix A.

Figure 7A:
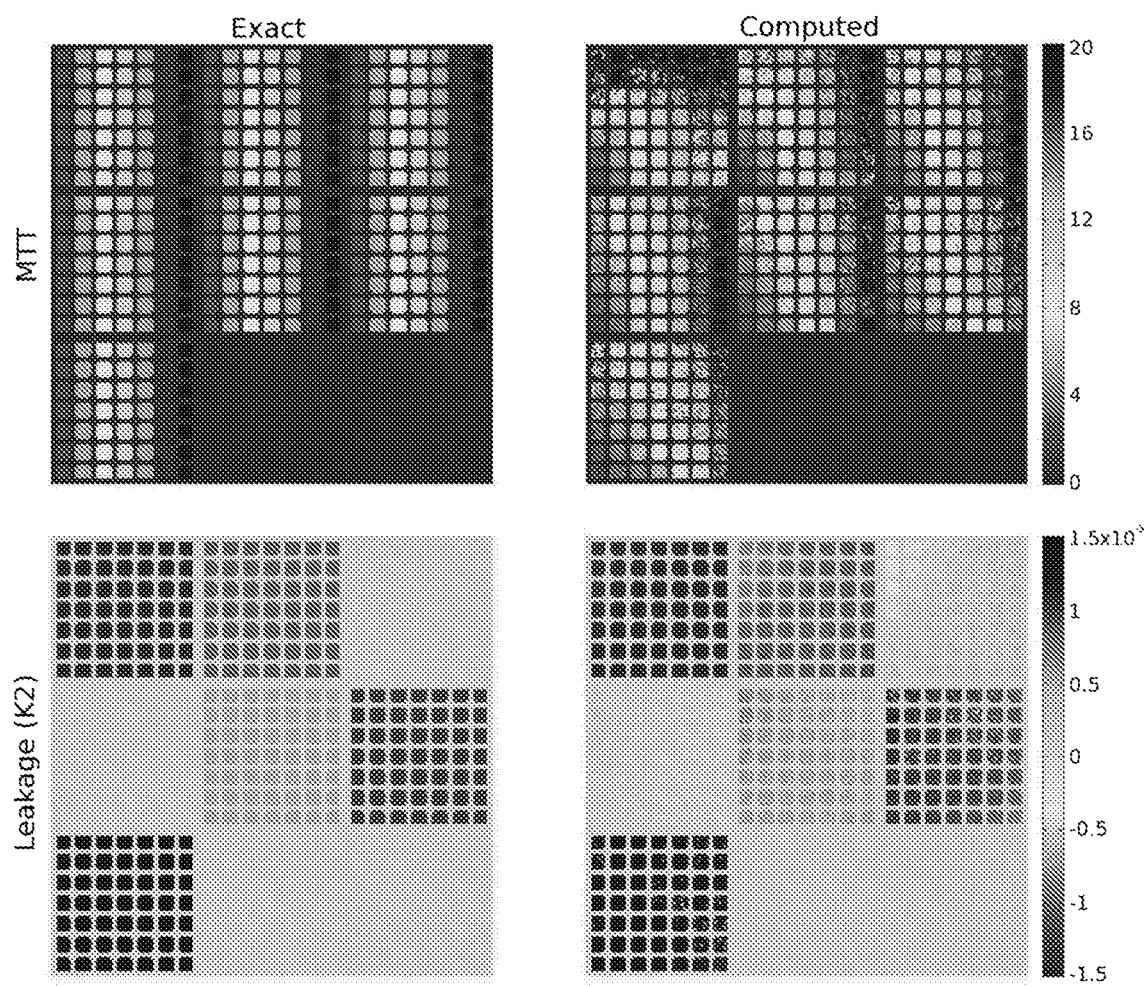
FIG. 7A shows MIT maps resulting from applying the algorithm according to the present invention, including the leakage term, to a phantom with different levels of contrast agent leakage.
Figure 7B:
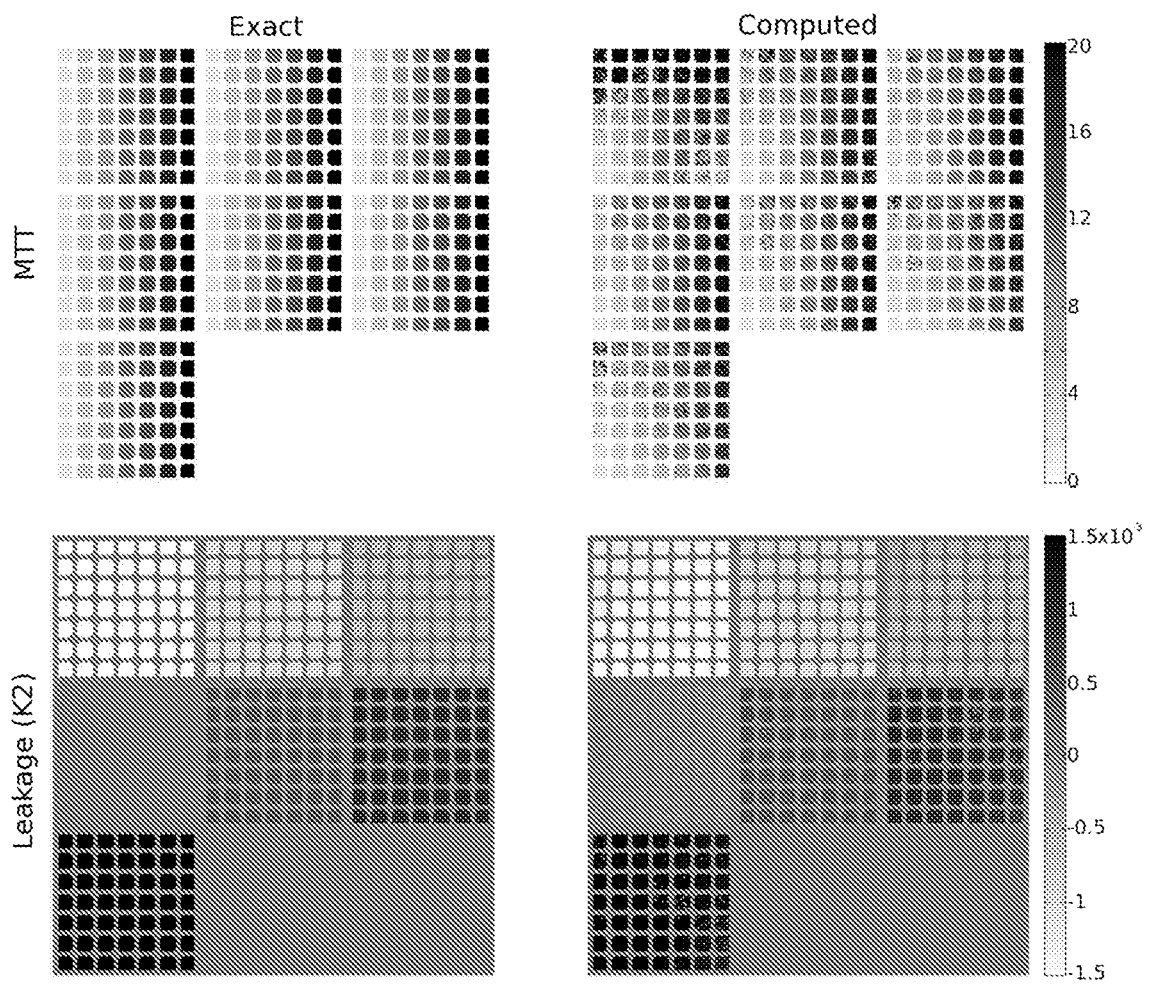
FIG. 7B is the corresponding grey scale version of the coloured FIG. 7A.

FIG. 7A shows MTT maps resulting from applying the algorithm according to the present invention, including the leakage term, to a phantom with different levels of contrast agent leakage. In the left column, the exact maps are presented for the MIT parameter (upper panel) and the leakage parameter K2 (lower panel), while the similar estimated maps are presented in the right column. The unit of the MTT maps is seconds, while the leakage parameter is Hertz (inverse seconds). FIG. 7B is the corresponding grey scale version of the coloured FIG. 7A.

Leakage is relevant for breakdown, puncture, or perforation of the blood-brain-barrier or loss of integrity of the tight endothelial junctions. It is also relevant to the kinetics of tissue outside the central nervous system, where no blood-brain barrier exists.

Figure 9:
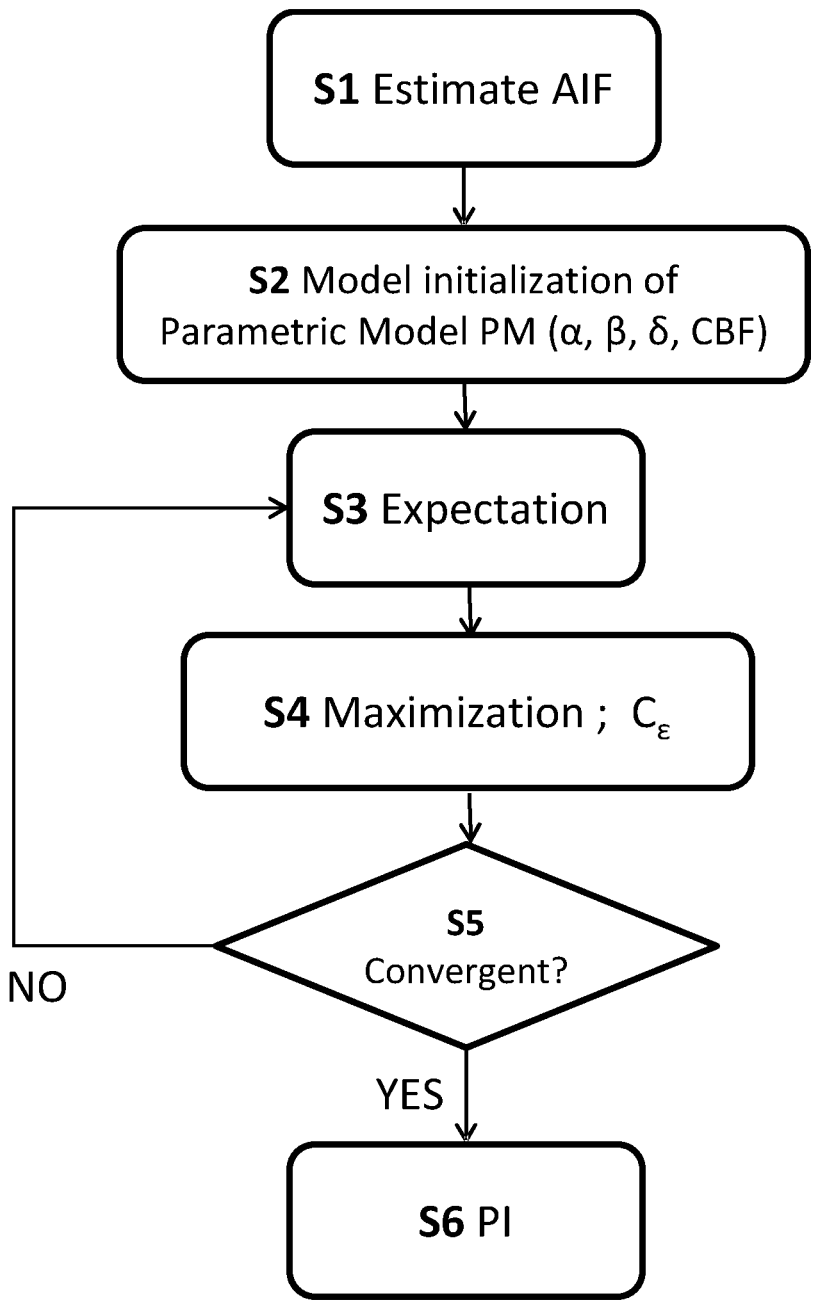
FIG. 9 is a schematic flow chart representing an out-line of details in the method or computer program product according to the invention.

FIG. 9 is a schematic flow chart representing an out-line of details in the method or computer program product according to the invention. The method for estimating perfusion indices PI in a mammal 200 comprises the steps of:
S1 Estimating an arterial input function AIF
S2 Applying a parametric model PM for capillary transit time distributions as a function of time based on obtained data DAT and DAT' representative of a contrast agent concentration as a function of time of an injected contrast agent
S3 Applying an expectation step of expectation-maximization (EM) type procedure
S4 Applying a maximization step of expectation-maximization (EM) type procedure with an exact analytical expression for the variance of an observation error of the contrast agent ($C_\epsilon$) in a non-linear observation model for the contrast agent concentration
S5 Determining whether the EM type procedure is convergent, e.g. by comparing to a convergence condition, such as $\epsilon_{thr}$, and if the EM procedure is not convergent, performing the step S3 and S4 again, and if the EM procedure of step S3 and S4 is convergent according to the convergence condition, then
S6 Estimate, and optionally display or store, perfusion indices PI.

In short, the present invention relates to a method for estimating perfusion indices PI in a mammal 200, e.g. a human. Data, DAT and DAT', representative of a contrast agent concentration as a function of time of an injected contrast agent is obtained from a medical imaging system 100, cf. FIG. 8. Perfusion indices PI are found by applying a parametric model PM for capillary transit time distributions as a function of time, and a minorize-maximization (MM) type procedure, such as an expectation-maximization (EM) type procedure, with regularization. The minorize-maximization type procedure has an exact analytical expression for the variance of an observation error of the contrast agent, $C_\epsilon$, in a non-linear observation model for the contrast agent concentration used in the maximization step. Clinical tests performed for 7 patients, cf. FIG. 6, show improved MTT mapping as compared to singular value decomposition (SVD), and reduced sensitivity to delay.

REFERENCES

Dempster, A. P., Laird, N. M., Rubin, D. B., 1977. Maximum likelihood from in-complete data via the EM algorithm. J. Royal Stat. Soc. B 39 (1), 1-38.
Jespersen, S. N., ⌊stergaard, L., 2012. The roles of cerebral blood flow, capillary transit time heterogeneity, and oxygen tension in brain oxygenation and metabolism. J Cereb Blood Flow Metab 32, 264-277.
Kenneth Lange, *Numerical Analysis for Statisticians*, 2010, Springer.
Mouridsen, K., Friston, K., Hjort, N., Gyldensted, L., ⌊stergaard, L., Kiebel, S., 2006. Bayesian estimation of cerebral perfusion using a physiological model of microvasculature. NeuroImage 33 (2), 570-579.
⌊stergaard, L., Aamand, R., Gutierrez-Jimenez, E., Ho, Y.-L., Blicher, J. U., Madsen, S. M., Nagenthiraja, K., Dalby, R. B., Drasbek, K. R., Møller, A., Brændgaard, H., Mouridsen, K., Jespersen, S. N., Jensen, M. S., West, M. J., 2012. The capillary dysfunction hypothesis of alzheimer's disease. Neurobiol Aging Submitted.
⌊stergaard, L., Jespersen, S. N., Mouridsen, K., Mikkelsen, I. K., Jonsdottir, K., Tietze, A., Blicher, J. U., Aamand, R., Hjort, N., Iversen, N. K., Cai, C., Hougaard, K. D., Simonsen, C. Z., Von Weitzel-Mudersbach, P., Modrau, B., Nagenthiraja, K., Riisgaard Ribe, L., Hansen, M. B., Bekke, S. L., Dahlman, M. G., Puig, J., Pedraza, S., Serena, J., Cho, T. H., Siemonsen, S., Thomalla, G., Fiehler, J., Nighoghossian, N., Andersen, G., May 2013a. The role of the cerebral capillaries in acute ischemic stroke: the extended penumbra model. J. Cereb. Blood Flow Metab. 33 (5), 635-648.

The above listed references are hereby incorporated by reference in their entirety.

The invention can be implemented by means of hardware, software, firmware or any combination of these. The invention or some of the features thereof can also be implemented as software running on one or more data processors and/or digital signal processors.

The individual elements of an embodiment of the invention may be physically, functionally and logically implemented in any suitable way such as in a single unit, in a plurality of units or as part of separate functional units. The invention may be implemented in a single unit, or be both physically and functionally distributed between different units and processors.

Although the present invention has been described in connection with the specified embodiments, it should not be construed as being in any way limited to the presented examples. The scope of the present invention is to be interpreted in the light of the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. A method for estimating perfusion indices (PI) in a mammal by a processor, the method comprising:
obtaining data (DAT, DAT') representative of a contrast agent concentration as a function of time of an injected contrast agent, and
estimating perfusion indices by:
applying a parametric model (PM) for capillary transit time distributions as a function of time on the obtained data, and
applying a minorize-maximization (MM) type procedure to the data, with regularization for estimating of the perfusion indices by an optimization,
wherein the minorize-maximization type procedure, comprises an exact analytical expression for the variance of an observation error of the injected contrast agent ($C_\epsilon$) in a non-linear observation model for the contrast agent concentration used in the maximization step.

2. The method according to claim 1, wherein the parametric model (PM) for capillary transit time distributions as a function of time comprises at least two parameters, the model further being defined for positive, or zero, transit times.

3. The method according to claim 1, wherein the parametric model (PM) for capillary transit time distributions as a function of time is selected from the group consisting of: gamma distribution, F-distribution, inverse Gaussian distribution, Gaussian distribution, half-normal distribution, Rayleigh distribution, Weibull distribution, negative binomial distribution, Poisson distribution, and Boltzmann distribution, or any combinations thereof.

4. The method according to claim 1, wherein the parametric model (PM) for capillary transit time distributions is a gamma-type function as a function of time (I'(t)) so as to enable estimation of a residue function, R(t).

5. The method according to claim 1, wherein the non-linear observation model for the contrast agent concentration ($y_t$) over time comprises a first (f) component and second component ($\epsilon$), the first term representing the product of the blood flow, and the tissue concentration ($C_a$) folded with the residue function, and the second term representing the observation error thereof ($\epsilon_t$), respectively.

6. The method according to claim 5, wherein the nonlinear observation model for the contrast agent concentration ($y_t$) over time further comprises a third term representing a leakage component of contrast agent over time from vascular to extravascular and extracellular space.

7. The method according to claim 5, wherein the nonlinear observation model has the form:

$$y_t = f(C_a(t), \theta) + \epsilon_t$$

$$\theta = \eta_\theta + \epsilon_\theta$$

where
$y_t$ is the non-linear observation model for the contrast agent concentration,
$\theta$ is a parameter being a function of the blood flow,
$C_a$ is tissue concentration, $\alpha$ is a first parameter of the parametric model,
$\beta$ is a second parameter of the parametric model,
$\epsilon_t$ is observation error, and
$\delta$ is a time delay representative of the delay between the site of measurement of $C_a$ and the site of measurement of $y_t$.

8. The method according to claim 7, wherein a linearization of the non-linear observation model is performed according to:

$$f(C_a(t), \theta) \approx \tilde{f}(\theta) = f(\hat{\theta}^{(i)}) + J(\theta - \hat{\theta}^{(i)})$$

where
J is a Jacobian function, and $$J = \frac{\partial}{\partial \theta} f(\hat{\theta}^{(i)}).$$

9. The method according to claim 8, wherein the residual, r, is defined as $$r = y - f(\hat{\theta}^{(i)}) + J\hat{\theta}^{(i)},$$

where
r is the residual,
y again denotes the contrast agent concentration curve, and where $$r = J\theta + \epsilon$$

$$\theta = \eta_\theta + \epsilon_\theta$$

so that the distribution of y is a statistical linear model.

10. The method according to claim 9, wherein one or more parameters of the statistical linear model are estimated using a minorize-maximize (MM) type procedure, so as to optimize a function related to perfusion.

11. The method according to claim 10, wherein the said function is the posterior probability and the convergence of the minorize-maximize (MM) type procedure, is monitored so as to assess the choice of prior distributions of parameters of the statistical linear model.

12. The method according to claim 10, wherein minorization is obtained using the expected value of a function:

$$E\text{-step: } Q(C_\epsilon) = \mathbb{E}_{q(\theta|y)} \ln p(\theta, y \mid C_\epsilon)$$

$$M\text{-step: } \underset{C_\epsilon}{\text{argmax}} Q(C_\epsilon)$$

where

Q is an orthogonal matrix.

13. The method according to claim 10, where the variance of an observation error of the contrast agent ($C_\varepsilon$) is functional dependent at least on J, $C_{\theta|y}$, and the residual r.

14. The method according to claim 13, wherein the variance of an observation error of the contrast agent ($C_\varepsilon$), under the assumption that $C_\varepsilon = \sigma^2 I$, can be written:

$$\sigma^2 N = tr(JC_{\theta|y}J') + (r - J\eta_{\theta|y})'(r - J\eta_{\theta|y})$$

where

σ is variance, and

N is the number of contrast agent concentration measurements.

15. The method according to claim 1, wherein the method further estimates a perfusion index indicative of the heterogeneity of the blood flow in a capillary bed of the mammal.

16. The method according to claim 1, wherein the method further estimates a perfusion index indicative of an extraction capacity (EC) of a substance, from the blood in a capillary bed of the mammal.

17. A medical imaging system for estimating perfusion indices in an associated mammal, the system comprising:
an imaging modality for obtaining data representative of contrast agent kinetics of an injected contrast agent, and storage means for optionally storing said data, and
a processor configured to estimate perfusion indices by obtaining data representative of a contrast agent concentration as a function of time of an injected contrast agent, and estimating perfusion indices by:
applying a parametric model (PM) for capillary transit time distributions as a function of time on the obtained data, and
applying a minorize-maximization (MM) type procedure to the data, with regularization for estimating of the perfusion indices by an optimization,
wherein the minorize-maximization type procedure, comprises an exact analytical expression for the variance of an observation error of the injected contrast agent ($C_\varepsilon$) in a nonlinear observation model for the contrast agent concentration used in the maximization step.

18. A computer program product being adapted to enable a computer system comprising at least one computer having data storage means in connection therewith to control an imaging modality and/or imaging medical system for estimating perfusion indices in an associated mammal by applying a method according to claim 1.

19. The method according to claim 4, wherein the parametric model (PM) for capillary transit time distributions is the form:

$$h(t \mid \alpha, \beta) = -\frac{dR}{dt} = \frac{1}{\beta^\alpha \Gamma(\alpha)} t^{\alpha-1} e^{-t/\beta},$$

where

R(t) is the residue function, t is time,

α is a first parameter, and

ß is a second parameter.

20. The method according to claim 5, wherein the first term represents cerebral blood flow (CBF).

21. The method according to claim 7, wherein the blood flow is cerebral blood flow (CBF).

22. The method according to claim 16, wherein the substance is oxygen (OEC, OEF) and/or glucose.

* * * * *